US011162932B2

(12) United States Patent
Dong et al.

(10) Patent No.: US 11,162,932 B2
(45) Date of Patent: Nov. 2, 2021

(54) SPECTROSCOPIC EVALUATION OF EDIBLE OIL USING PROFILES

(71) Applicant: Cargill, Incorporated, Wayzata, MN (US)

(72) Inventors: Jinping Dong, Shoreview, MN (US); Steven Hansen, Chanhassen, MN (US); Jacob Schaller, Chaska, MN (US); Sean Smith, Minneapolis, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 16/719,667

(22) Filed: Dec. 18, 2019

(65) Prior Publication Data
US 2020/0124582 A1  Apr. 23, 2020

Related U.S. Application Data

(63) Continuation of application No. PCT/US2019/040571, filed on Jul. 3, 2019.
(Continued)

(51) Int. Cl.
*G01N 33/03* (2006.01)
*G01J 3/42* (2006.01)

(52) U.S. Cl.
CPC .............. *G01N 33/03* (2013.01); *G01J 3/42* (2013.01); *G01J 2003/425* (2013.01)

(58) Field of Classification Search
CPC ........ G01N 27/24; G01N 27/06; G01N 27/20; G01N 33/03; G01J 3/42
See application file for complete search history.

(56) References Cited

U.S. PATENT DOCUMENTS 6,600,306 B1 * 7/2003 Pernot ................ A47J 37/1266
324/423
6,822,461 B2 * 11/2004 Klun .................... G01N 27/226
324/698
(Continued)

FOREIGN PATENT DOCUMENTS

IN   1366del2014 A   8/2016
JP   2018205226 A   12/2018
(Continued)

OTHER PUBLICATIONS

Bordi, Peter, et al., "French Fry Testing Soybean Oil Filtered Vs unfiltered Canola Oil Filtered vs Unfiltered Final Presentation", AOCS Annual Meeting & Expo, (2018), 39 pgs.
(Continued)

*Primary Examiner* — Steven N Leff

(57) ABSTRACT

A characteristic of edible oil may be evaluated using a spectrometer. For example, optical reflectance data may be obtained from edible oil in situ in a frying apparatus housing the edible oil, the reflectance data corresponding to a specified range of infra-red wavelengths. A model profile corresponding to the characteristic being assessed may be obtained, such as from a repository housing a secured library of such profiles. The model profile may define a regression vector for use in transforming the reflectance data to generate a value corresponding to the characteristic being assessed. A criterion may be applied to the value to establish a simplified representation of the characteristic for presentation to a user for assessment of oil quality.

20 Claims, 15 Drawing Sheets

Related U.S. Application Data

(60) Provisional application No. 62/695,444, filed on Jul. 9, 2018.

(56) References Cited

U.S. PATENT DOCUMENTS

| | | | |
|---|---|---|---|
| 7,329,547 | B2 | 2/2008 | Azizian |
| 7,504,836 | B2 * | 3/2009 | Chambon ............ A47J 37/1266 324/686 |
| 8,497,691 | B2 | 7/2013 | Behle et al. |
| 9,228,965 | B2 * | 1/2016 | Burkett ............... A47J 37/1266 |
| 9,945,829 | B2 | 4/2018 | Brugger |
| 2009/0252842 | A1 | 10/2009 | Wang et al. |
| 2011/0129578 | A1 | 6/2011 | Feinberg et al. |
| 2015/0027205 | A1 | 1/2015 | Brugger |
| 2016/0299061 | A1 | 10/2016 | Goldring et al. |
| 2017/0138883 | A1 * | 5/2017 | Lambert ............. A47J 37/1271 |
| 2017/0160131 | A1 | 6/2017 | Goldring et al. |
| 2017/0292908 | A1 * | 10/2017 | Wilk .................... G01J 3/0289 |
| 2018/0052144 | A1 * | 2/2018 | Azizian ................. G01N 33/03 |
| 2018/0116459 | A1 | 5/2018 | Lin et al. |
| 2018/0125299 | A1 | 5/2018 | Mcghee et al. |

FOREIGN PATENT DOCUMENTS

| | | | | |
|---|---|---|---|---|
| WO | WO-2009080049 | A1 * | 7/2009 | ......... G01N 21/3577 |
| WO | WO-2015142283 | A1 | 9/2015 | |
| WO | WO-2016141451 | A1 * | 9/2016 | ............ G01N 33/03 |
| WO | WO-2020014073 | A1 | 1/2020 | |
| WO | WO-2020139952 | A1 | 7/2020 | |

OTHER PUBLICATIONS

Iassonova, Diliara, "Evolution of frying oils: from fast heat transfer to stability, flavor and nutrition", 9th International Symposium on Deep-Fat Frying, (Oct. 30, 2017), 27 pgs.

Iassonova, Diliara, "Safety Aspects of Frying Oils" Academia and Industry Perspectives, AOCS Annual Meeting & Expo, (2018), 12 pgs.

"International Application Serial No. PCT/US2019/040571, International Search Report dated Oct. 9, 2019", 2 pgs.

"International Application Serial No. PCT/US2019/040571, Written Opinion dated Oct. 9, 2019", 7 pgs.

"Testo 270—Cooking oil tester", Order-Nr. 0563 2750, Testo SE & Co. KGaA, [Online], Retrieved from the Internet: <URL: https://www.testo.eom/en-UK/testo-270/p/0563-2750>, (Accessed Jun. 22, 2018), 4 pgs.

Al-Alawi, Ahmed, et al., "New FTIR Method for the Determination of FFA in Oils", J Am Oil Chem Soc 81(5), (2004), 441-6.

Allendorg, Meghan, "Application of a Handheld Portable Infrared Sensor to Monitor Oil Quality", A Thesis Presented in Partial Fulfillment of the Requirements for the Degree Masters of Science in the Graduate School of The Ohio State University, (2010), 113 pgs.

Aykas, Didem, et al., "Assessing potato chip oil quality using a portable infrared spectrometer combined with pattern recognition analysis", The Royal Society of Chemistry. Anal. Methods, 8, [Online], Retrieved from the Internet: <URL: http://pubs.rsc.org/-/content/articlelanding/2016/ay/c5ay02387d/unauth#!divAbstract>, (2016), 731-741.

Birkel, Emily, "Application of a Portable Handheld Infrared Spectrometer for Quantitation of trans Fat in Edible Oils", A Thesis Presented in Partial Fulfillment of the Requirements for the Degree Master of Science. In Journal of the American Oil Chemists' Society 88(10), (2011), 82 pgs.

Kempen, T A, et al., "Infrared Spectroscopy as a Tool for Assessing Fat Quality", Poultry Science Association, Inc., [Online], Retrieved from the Internet: <URL: https://academic.oup.com/japr/article-abstract/11/2/191/713524>, (2002), 191-201.

Kress-Rogers, Erika, et al., "Development and evaluation of a novel sensor for the in situ assessment of frying oil quality", Food Control 1.3, (Jul. 1, 1990), 163-178.

Ma, Jin-Kui, "Studies on the Frying Stability and Quick Quality Evaluation Method of Local Rapeseed Kizakinonatane Oil", A Dissertation Presented to The Graduate School of Bioresource Sciences in Partial Fulfillment of the Requirements for the Degree of Doctor of Philosophy, (Sep. 2014), 183 pgs.

Ng, Cl, "Method for Determining Frying Oil Degradation by Near-Infrared Spectroscopy", J Agric Food Chern. 55(3), [Online], Retrieved from the Internet: <URL: https://www.ncbi.nlm.nih.gov/pubmed/17263446, (2007), 593-7.

"International Application Serial No. PCT/US2019/040571, International Preliminary Report on Patentability dated Jan. 21, 2021", 9 pgs.

"International Application Serial No. PCT/US2019/068587, International Search Report dated Mar. 10, 2020", 2 pgs.

"International Application Serial No. PCT/US2019/068587, Written Opinion dated Mar. 10, 2020", 19 pgs.

* cited by examiner

| SITE | UNIT | TIMESTAMP | α | β | RESULT |
|---|---|---|---|---|---|
| MAYBERRY | 1 | 01-MAY-2018 20:14 | x.y | z.p | FILTER |
| MAYBERRY | 1 | 01-MAY-2018 10:05 | x.y | z.p | OK |
| MAYBERRY | 2 | 01-MAY-2018 8:04 | x.y | z.p | DISCARD |
| MAYBERRY | 3 | 01-MAY-2018 7:55 | x.y | z.p | FILTER |
| MAYBERRY | 3 | 29-APR-2018 5:05 | x.y | z.p | OK |
| . | | | | | |
| . | | | | | |
| . | | | | | |
| SPRINGFIELD | 1 | 29-APR-2018 11:30 | x.y | z.p | FILTER |
| SPRINGFIELD | 2 | 29-APR-2018 11:35 | x.y | z.p | OK |
| SPRINGFIELD | 3 | 28-APR-2018 16:22 | x.y | z.p | OK |
| SPRINGFIELD | 4 | 28-APR-2018 18:45 | x.y | z.p | OK |
| SPRINGFIELD | 4 | 27-APR-2018 18:30 | x.y | z.p | DISCARD |

SPECTROSCOPIC EVALUATION OF EDIBLE OIL USING PROFILES

CLAIM OF PRIORITY

This patent application is a continuation of Dong et al., PCT Application Number PCT/US2019/040571, titled "SPECTROSCOPIC EVALUATION OF EDIBLE OIL USING PROFILES," filed Jul. 3, 2019, which claims the benefit of priority of Dong et al., U.S. Provisional Patent Application No. 62/695,444, titled "SYSTEM AND TECHNIQUES FOR NEAR-INFRARED SPECTROSCOPIC EVALUATION OF EDIBLE OIL USING PROFILES," filed on Jul. 9, 2018, the benefit of priority of each of which is hereby presently claimed, and each of which is hereby incorporated by reference herein in its entirety.

FIELD OF THE DISCLOSURE

This document pertains generally, but not by way of limitation, to near-infrared spectroscopy, and more particularly, to simplifying spectroscopic evaluation of edible oils, such as to facilitate measurement in situ in a fryer or food preparation environment.

BACKGROUND

Food scientists employ a variety of analytical tools to assist in quantitative evaluation of various characteristics of products, from raw materials to finished goods. Generally, analytical tools may rely upon careful control and preparation of a sample for evaluation, such as according to a standardized test or evaluation protocol in a "bench" setting. In this manner, traceable and repeatable results may be obtained. Examples of such techniques, such as may be applied to edible oils, include Fourier Transform (FT) Infra-red (IR) Spectroscopy, Nuclear Magnetic Resonance (NMR), Gel Permeation Chromatography (GPC), and Gas Liquid Chromatography (GLC), as illustrative examples. Use of analytical techniques to evaluate edible oils helps to verify or maintain quality throughout the production and distribution process. For example, after processing, bench analytical techniques may be used to verify that minor components, such as free fatty acid, are at or below specified levels. Analytical techniques may also be used to assess edible oils for a presence of contaminants or adulterants.

SUMMARY OF THE DISCLOSURE

Edible oils used for frying food, such as in deep fat frying applications, undergo a variety of degradation mechanisms as such oils age in use. Such degradation mechanisms may adversely impact oil quality, and may include oxidative processes, hydrolysis, and pyrolysis, as illustrative examples. Edible oils used for frying may be subject to an end-use monitoring regime (e.g., subject to regulatory requirements), and such requirements may be specific to particular geographic locales. Such requirements may be specified in terms of limits relating to polar material (e.g., Total Polar Material (TPM)), free fatty acid (FFA) content, color (e.g., Gardner color unit), or polymer content, as illustrative examples. The present inventors have recognized, among other things, that testing, logging, and analyzing parameters relating to edible oils in actual use scenarios may present various challenges. For example, bench analytical techniques may provide robust repeatability for evaluation of samples, but sample preparation may be cumbersome and may not generally provide results in real-time or near-real-time. Moreover, use of bench analytical techniques may involve specialized skills in sample preparation, sample handling, execution of tools for quantitative analysis, and reporting of results. Even if the sampling process were simplified, unskilled personnel may have difficulty in interpreting results reported quantitatively in terms of TPM, FFA, a color metric, a polymer content, or other technical parameters.

In another approach, an electrical technique may be used to estimate oil degradation, such as using a capacitive sensor immersed in the edible oil. By contrast, use of a spectroscopy technique (e.g., reflectance spectroscopy) as described herein allows a user to optically probe an edible oil in situ (e.g., in a fryer tank and at operating temperature) without requiring contact between the sensor assembly (such as a hand-held assembly) and the oil.

The present inventors have also recognized that TPM, FFA, or other parameters, when viewed in isolation, may provide an indication of oil quality such as to trigger activity such as filtering the oil or replacing it, but such parameters alone may not provide indicia of a likely overall quality of food prepared using the oil. Indicia of food quality are generally specified subjectively in terms of flavor, texture, aroma, or combinations thereof. The present inventors have recognized that a combination of analytically-determined parameters may be used to evaluate both oil quality and to predict resulting food quality.

In an example, a technique such as a method may include spectroscopic evaluation of a characteristic of edible oil. In particular, the technique may include, using a spectrometer, optically obtaining reflectance data from the edible oil in situ in a frying apparatus housing the edible oil, the reflectance data corresponding to a specified range of infra-red wavelengths, obtaining a secured model profile corresponding to the characteristic being assessed, transforming the reflectance data using the model profile to generate a value corresponding to the characteristic, and applying a criterion to the value to establish a simplified representation of the characteristic for presentation to a user for assessment of oil quality. In an example, the technique may include transmitting the value to another device for at least one of presentation or storage.

In an example, a system may be used for spectroscopic evaluation of a characteristic of edible oil. The system may include a spectrometer configured to emit light comprising a specified range of infra-red wavelengths, receive a reflection from edible oil in situ in a frying apparatus housing the edible oil, and establish reflectance data corresponding to the received reflection. In an example, the system may include a processor circuit coupled to a memory circuit and communicatively coupled to the spectrometer, the processor circuit configured to securely obtain a model profile corresponding to the characteristic being assessed and to store the model profile in the memory circuit, transform the reflectance data obtained using the spectrometer, using the model profile to generate a value corresponding to the characteristic, and apply a criterion to the value to establish a simplified representation of the characteristic for presentation to a user for assessment of oil quality.

This summary is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As mentioned above, the present inventors have recognized, among other things, that spectroscopy may be used to characterize edible oils in situ, such as using a reflectance spectroscopy technique in a near-infrared range of wavelengths. For example, a value of a characteristic of the edible oil may be determined, such as established using a model profile obtained from a repository in a secure manner.

Figure 1:
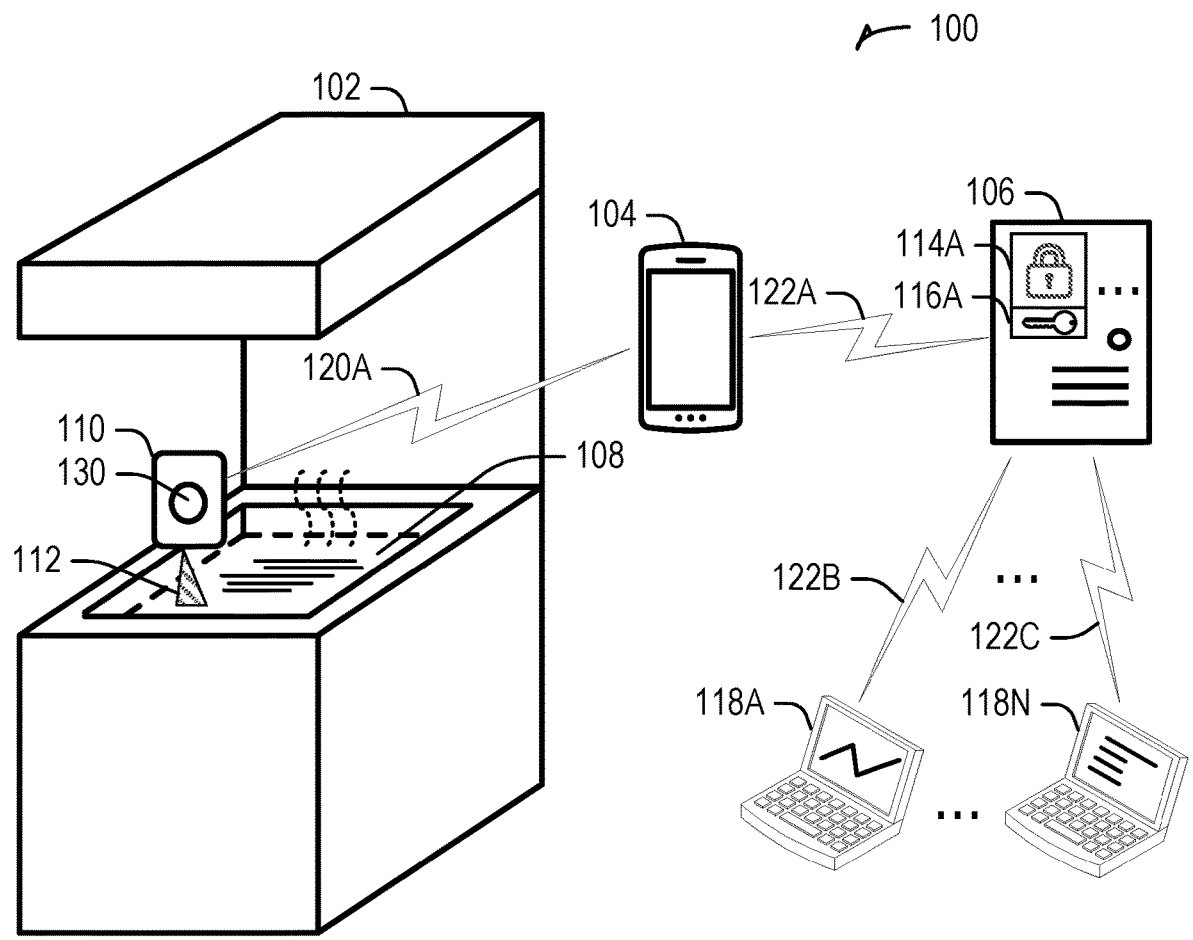
FIG. 1 illustrates generally an example showing a system that may include a spectrometer, such as for characterization of edible oil in situ.

FIG. 1 illustrates generally an example showing a system 100 that may include a spectrometer 110, such as for characterization of edible oil 108 in situ, such as within a tank of a frying apparatus 102 (e.g., a commercial deep fat fryer). Evaluation of a characteristic of the edible oil 108 may be performed with the oil at normal operating temperature (e.g., 350 degrees Fahrenheit). The spectrometer 110 may include a user interface 130, such as including a user input and a display, as mentioned in relation to other examples described herein. The spectrometer 110 may be portable, such as sized and shaped to be manipulated by a user by hand. The spectrometer may be configured to emit light 112 comprising a specified range of infra-red wavelengths, and to receive a reflection from edible oil 108 in situ in a frying apparatus 102 housing the edible oil. The spectrometer 110 may then establish reflectance data corresponding to the received reflection without requiring physical contact between the spectrometer 110 and the oil 108.

The spectrometer 110 may include a processor circuit configured to provide reflectance data comprising a series of values corresponding to discrete wavelength values spanning a specified range of wavelengths. As an illustrative example, the specified range may include wavelengths from about 700 nanometers to about 1100 nanometers. The spectrometer 110 may include a housing and hardware configuration similar to the SCiO apparatus (available from Consumer Physics, Tel Aviv, Israel), such as to provide reflectance data from a range of 750 nanometers to 1070 nanometers. The use of reflectance spectroscopy in the near-infrared range of wavelengths is illustrative, and other spectroscopic techniques may be used. The spectrometer 110 may be coupled via a wireless communication channel 120A to another device, such as a device 104 (e.g., a mobile device such as a cellular handset, a tablet device, a "phablet" device having a cellular or wireless networking adaptor, a laptop or desktop computer, or a base-station located in a facility housing the frying apparatus 102, as illustrative examples).

The wireless communication channel 120A may be established according to a wireless communication standard such as Bluetooth® (e.g., Bluetooth® Low Energy (BLE) as described in the Bluetooth Core Specification, v. 5.0, published Dec. 6, 2016, by the Bluetooth® Special Interest Group, Kirkland, Wash.) or according to one or more other standards (e.g., the Institute of Electrical and Electronics Engineers (IEEE) 802.11 family of standards known as Wi-Fi®, mobile communications standards such as relating to 4G/Long Term Evolution (LTE), or the IEEE 802.15.4 family of standards, as illustrative examples).

The device 104 may include one or more processor circuits coupled to one or more memory circuits. For example, the device 104 may be configured to transform received reflectance data provided by the spectrometer 110 such as using a model profile to generate a value of a characteristic being assessed. The device 104 may be coupled through another wireless communication channel 122A to a repository 106 such as a remotely-located server or a cloud-based (e.g., distributed) facility establishing the repository 106. For example, the wireless communication channel 122A may be established according to a wireless networking protocol mentioned above, or a digital cellular networking protocol, as illustrative examples. The repository 106 may include at least one secure model profile 114A (e.g., an encrypted model profile or a model profile that is otherwise access-controlled). In one approach, the device 104 may obtain the model profile 114A from the repository 106, such as in response to receiving a request or selection from the user either via the device 104 or a user interface associated with the spectrometer 110. The repository 106 or another device may store a key 116A corresponding to the encrypted model profile 114A. For example, a key 116A may be provided to a user to enable use of a model profile 114A in response to validation that the user is permitted to apply the model profile for use in transforming received reflectance data. Alternatively, or in addition, another verification scheme may be used such as to selectively permit access to an access-controlled model profile 114A. One or more criteria may be applied to the transformed reflectance data. For example, a value of a characteristic being assessed, such as a parameter relating to Free Fatty Acid (FFA), Total Polar Material (TPM), a color metric, or a polymer content, may then be used to establish a simplified representation of a status of the edible oil 108 for presentation to a user (such as shown illustratively in the examples shown and described in relation to FIG. 8). The simplified representation (e.g., a color code such as green or red) may be presented to the user via the user interface 130 of the spectrometer or the device 104 (e.g., via an edible oil management application running on the device 104), as illustrative examples.

In another example, the device 104 serves as an intermediary device, and the repository 106 (or other facility such as a cloud-based resource) may perform the transformation of the reflectance data to establish a value of the characteristic being assessed, such as using the model profile 114A and key 116A. In yet another example, the spectrometer 110 includes one or more processor circuits coupled to one or more memory circuits, and the device 104 need not be used. For example, the spectrometer 110 may transmit reflectance data to the repository 106 for processing (e.g., transformation), or the spectrometer 110 may securely receive the model profile 114A from the repository 106 and apply the model profile 114A to transform reflectance data.

In the examples described herein, one or more of the spectrometer 110 or the device 104 may one or more of transmit, store, or receive respective values of assessed characteristics relating to the edible oil 108, such as for purposes of trending, reporting, or auditing. For example, one or more client devices 118A through 118N may be used to obtain or generate reports or other data relating to a series of assessments performed using the spectrometer 110 (e.g., as shown illustratively in the examples of FIG. 10A or FIG. 10B), such as through communication channels 122B or 122C. The repository 106 may be implemented as a device (e.g., a server or a base-station) located at a single facility such as a restaurant or food production facility, or the repository 106 may be a remote server, such as serving multiple sites. A single spectrometer 110 may be used to assess a characteristic of edible oil 108 across multiple pieces of frying equipment, or multiple spectrometers may be used in communication with the repository 106, such as through respective devices such as a device 104. In this manner, edible oil management may be provided to support a variety of system 100 topologies at different operational scales, such as facilitated by an easy-to-use spectrometer 110 (e.g., a hand-held assembly) that may provide a simplified representation of a status of the edible oil 108 without requiring contact (e.g., immersion) in the edible oil 108.

Figure 2:
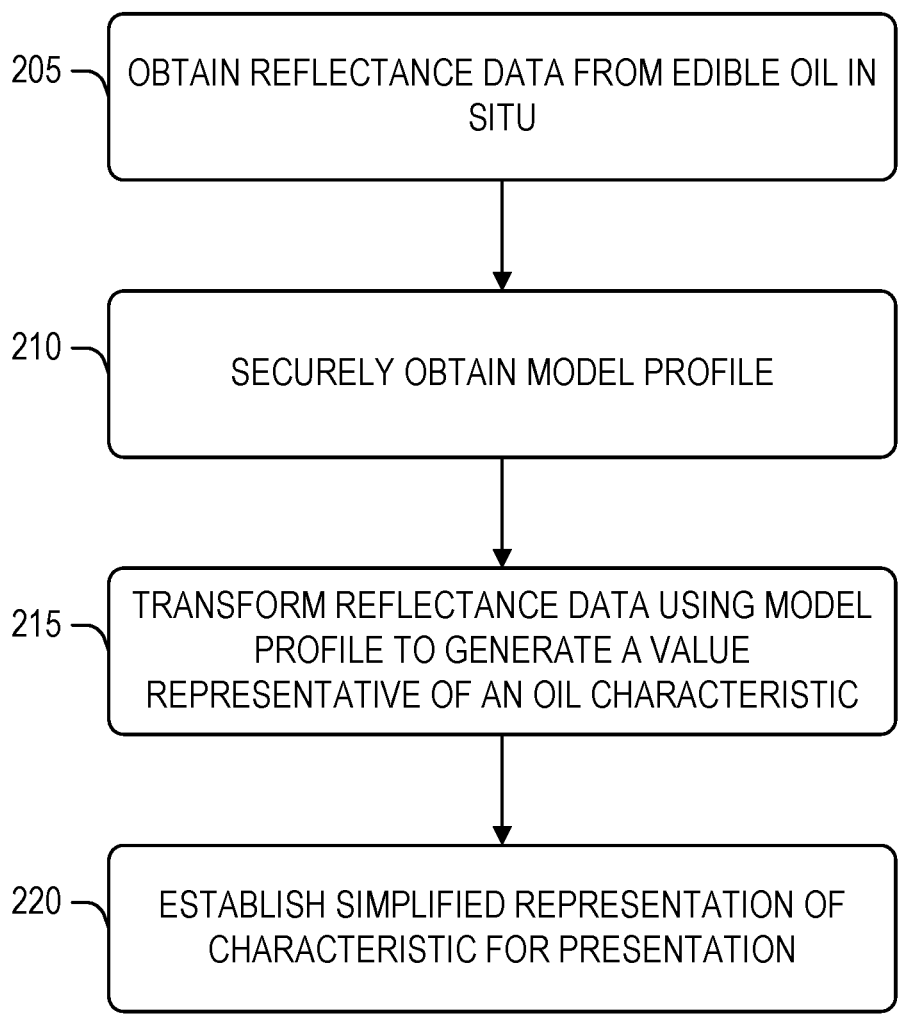
FIG. 2 illustrates generally an example comprising a technique, such as an automated method, including obtaining reflectance data from an edible oil in situ, using a spectrometer.

FIG. 2 illustrates generally an example comprising a technique 200, such as an automated method, including obtaining reflectance data from an edible oil in situ at 205, such as using a spectrometer. The use of reflectance data is illustrative, and other types of spectroscopy (e.g., absorption spectroscopy) could be used in relation to the technique 200 of FIG. 2 or in relation to other examples described herein. At 210, a model profile may be securely obtained. For example, upon initial configuration of a system comprising a spectrometer, an encrypted representation of a model profile may be received, such as in response to a user selection or according to a procedure in which a model profile is validated for use by a particular user. As an illustrative example, a spectrometer may be configured for use at a specified site or in relation to a specified vendor, and a corresponding model profile may be provided in a secure manner for use in assessing a desired characteristic (e.g., FFA, TPM, a color metric, a polymer content, etc.). Geographic variations may exist in terms of which characteristics are of interest to particular users, such as in view of regulatory considerations. A user may be inhibited from using a particular model if access-control limitations are not met, such as relating to oil type, geography, spectrometer type, or other criteria. In this manner, erroneous estimates of the desired characteristic may be avoided.

At 215, the reflectance data obtained at 205 may be transformed to generate a value representative of the characteristic being assessed. As mentioned in relation to other examples herein, such a characteristic may include one of a free fatty acid (FFA) value, a Gardner color unit, a total polar material (TPM) level, or a polymer content, as illustrative examples. As an illustration, the model profile may include a set of regression coefficients corresponding to or otherwise established using a partial least squares (PLS) regression model. The regression coefficients may correspond to wavelength-dependent weighting factors to be applied to corresponding reflectance values. In an example, the model profile may, when decrypted or otherwise enabled for use by a user, provide a vector that may be multiplied by a representation of the reflectance data to provide a scalar value representative of the characteristic being assessed. The resulting scalar value may be one or more of transmitted or stored, such as for reporting, trending, or auditing. The present inventors have also recognized, among other things, that a user (such as a line employee at a restaurant or maintenance personnel) may benefit from receiving a simplified representation of the characteristic being assessed. Such a simplified representation may be established using one or more criteria, such as via a threshold comparison or binning as discussed in relation to the illustrative examples of FIG. 9. Accordingly, at 220, the simplified representation may be established by applying a criterion to the value of the determined characteristic. The simplified representation may be presented to a user for assessment of oil quality.

Figure 3:
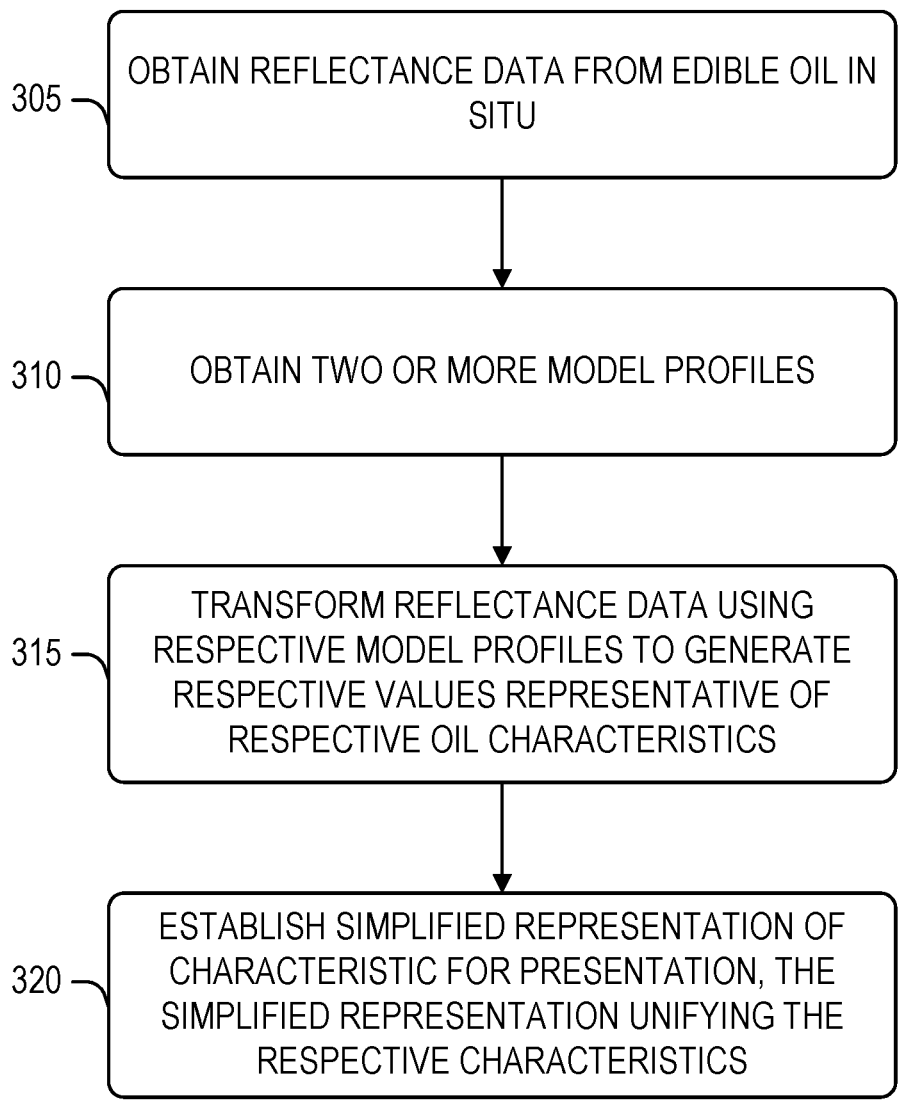
FIG. 3 illustrates generally an example comprising another technique, such as an automated method, including obtaining reflectance data from an edible oil in situ, using a spectrometer.

FIG. 3 illustrates generally an example comprising another technique 300, such as an automated method, including obtaining reflectance data from an edible oil in situ, using a spectrometer. As in the example of FIG. 2, in FIG. 3, at 305, reflectance data may be obtained from edible oil in situ, using a spectrometer. At 310, two or more model profiles may be securely obtained, such as corresponding to different edible oil characteristics to be assessed. At 315, the reflectance data obtained at 305 may be transformed using the two or more model profiles to generate respective values representative of respective oil characteristics. At 320, a simplified representation of the result of the transformations at 315 may be established, such as for presentation to the user. In this manner, the simplified representation established at 320 unifies results from the separate transformations performed at 315, as discussed below in relation to the illustrative examples of FIG. 9. The simplified representation determined at 320 may define a predictive assessment of a quality of food prepared using the edible oil from which the reflectance data was obtained at 305.

Figure 4:
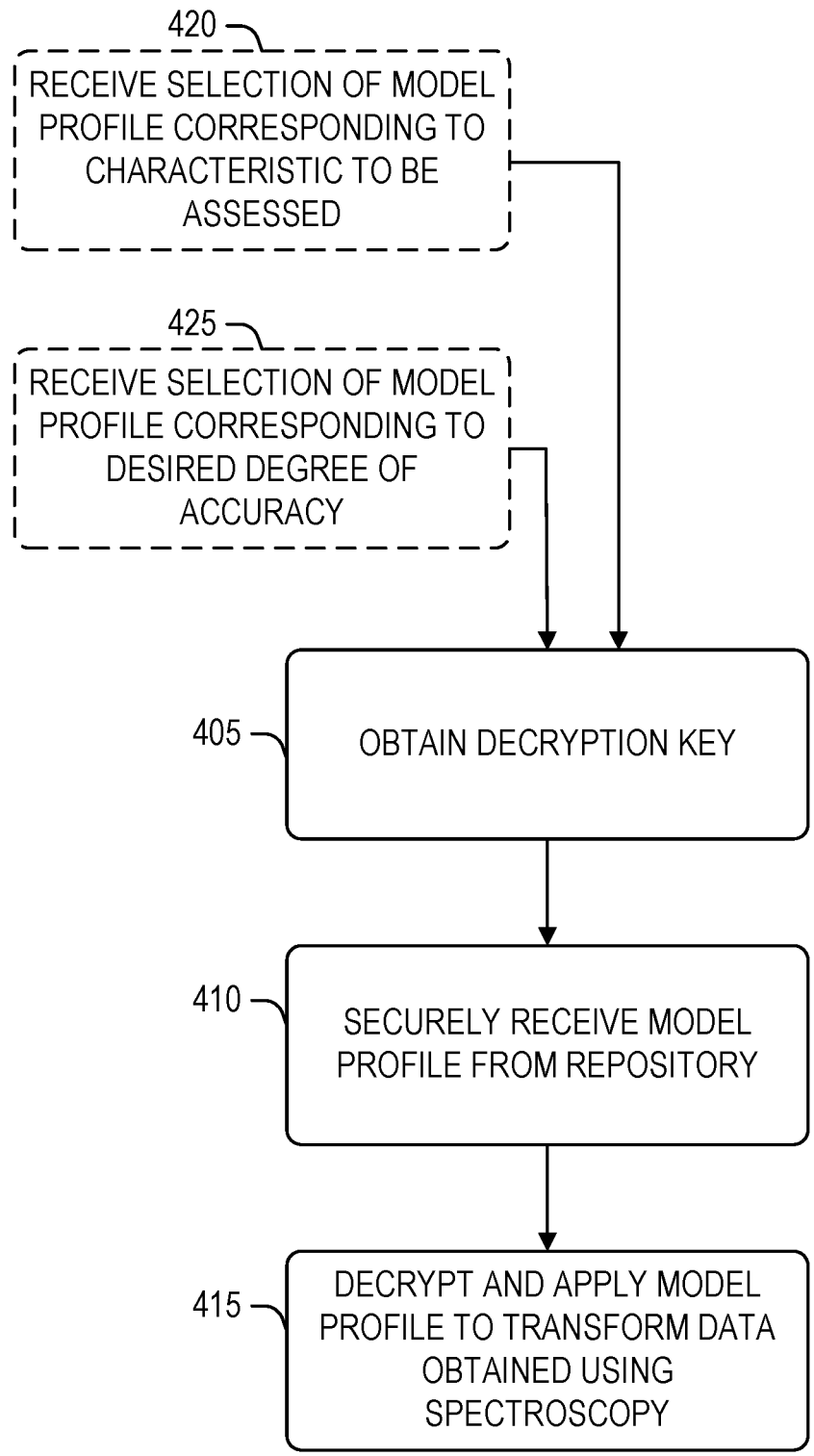
FIG. 4 illustrates generally an example comprising a technique, such as an automated method, including obtaining an decryption key, such as for use in applying a model profile to transform data obtained using spectroscopy.

FIG. 4 illustrates generally an example comprising a technique 400, such as an automated method, including obtaining a decryption key, such as for use in applying a model profile to transform data obtained using spectroscopy. At 405, a decryption key may be obtained (such as in response to a request from a user). The decryption key may include key data relating to a symmetric or asymmetric key infrastructure. For example, the decryption key may be specific to a particular model profile, a specific user or organization, a specific geography, or established in relation to other criteria (such as related to a type of edible oil being consumed). At 410, a model profile may be securely received, such as from a repository. The repository may house a library of different model profiles, such as for use in characterizing one or more different specified types of oil, such as canola oil, soybean oil, corn oil, or blends thereof (e.g., a canola oil, corn oil, and soybean oil blend). The different specified types of oil may also include high oleic oils comprising one or more of canola oil, corn oil, soybean oil, or blends thereof, as illustrative examples. For example, a secure session scheme may be used to transmit an encrypted representation of the model profile from the repository, using an internet protocol (IP) network. At 415, the model profile may be decrypted and then used to transform data obtained using spectroscopy. As mentioned above, the model profile may contain a vector defining regression coefficients to be applied to a representation of the reflectance data in order to transform the reflectance data from a raw or intermediate form to a calibrated value.

Optionally, the model profile to be securely received may be selected. For example, at 425, a selection from a user may be received corresponding to a desired accuracy level (e.g., with respect to a corresponding primary standard), and a corresponding model profile may be provided. For example, certain model profiles may be provided that are specific to one edible oil species, or a "universal" model may be selected to provide an estimate of the desired characteristic when used in relation to multiple oil species. For example, a "universal" model profile may provide a specified level of accuracy when used in relation to characterizing two or more different specified types of oil, such as canola oil, soybean oil, corn oil, or blends thereof (e.g., a canola oil, corn oil, and soybean oil blend). The different specified types of oil may also include high oleic oils comprising one or more of canola oil, corn oil, soybean oil, or blends thereof, as illustrative examples. In another example, optionally, at 420, a selection from a user may be received corresponding to a characteristic to be assessed (e.g., FFA, TPM, or other characteristics). Management of access to particular secure model profiles may be performed according to dynamic or pre-defined agreements (e.g., defining permissions for particular users to decrypt and apply a model profile). For example, access to certain model profiles providing characteristics relating to particular oil types or characteristics to be assessed may be managed on a subscription basis or according to geographical locale, as illustrative examples. Use of encrypted models may facilitate enforcement of specified service levels. For example, models may be certified or decertified based on specified date ranges or other criteria. If models are updated (such as mentioned below in relation to the example of FIG. 7), a prior revision of the model may be de-certified or otherwise deactivated.

Figure 5:
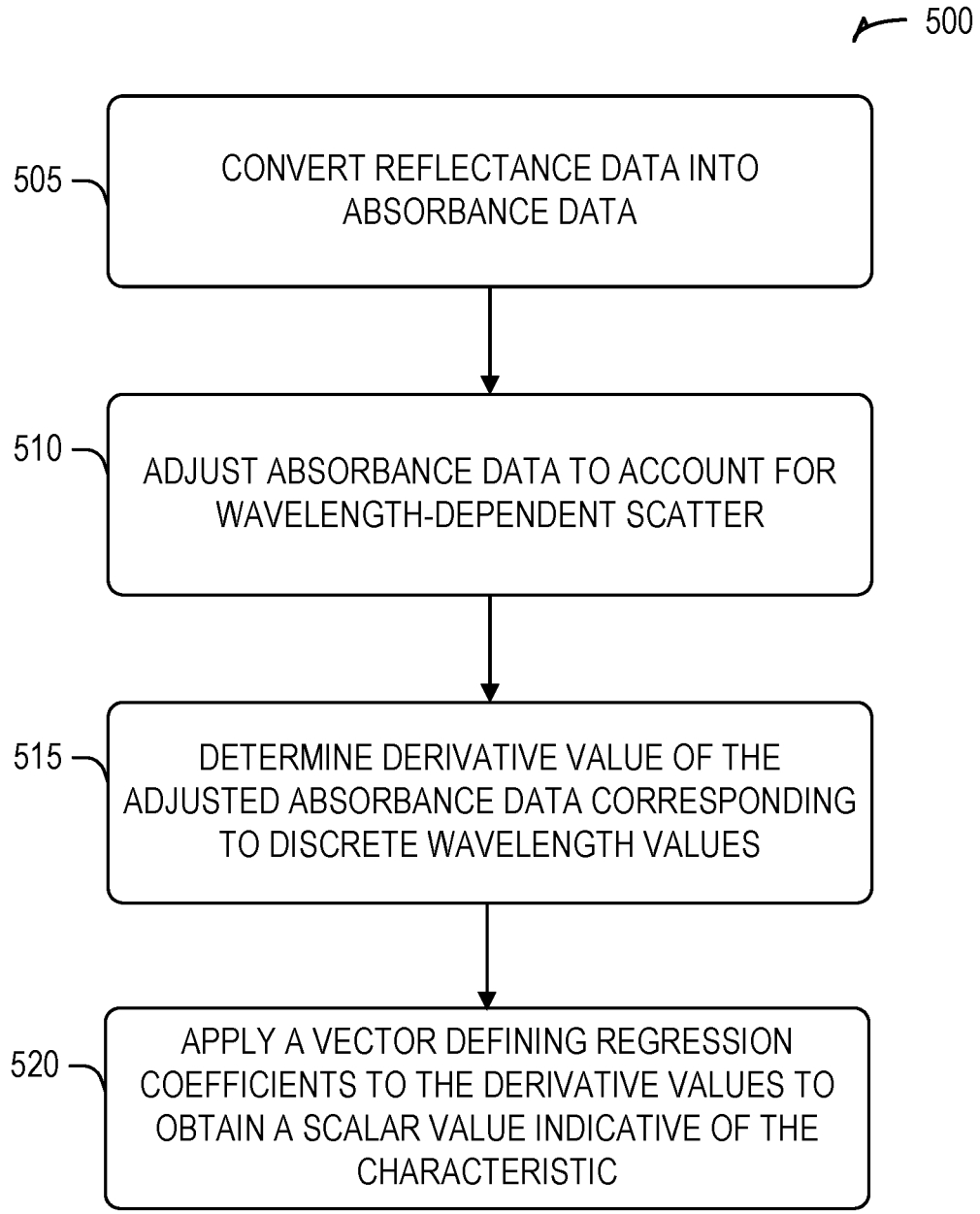
FIG. 5 illustrates generally an example comprising a technique, such as an automated method, including transforming data obtained using spectroscopy to obtain a value indicative of a characteristic of edible oil.

FIG. 5 illustrates generally an example comprising a technique 500, such as an automated method, including transforming data obtained using spectroscopy to obtain a value indicative of a characteristic of edible oil. As mentioned in relation to other examples herein, reflectance data may be obtained using a spectrometer. At 505, the reflectance data may be converted into equivalent absorbance data such as via applying an expression (e.g., $\log(1/R)$) to reflectance values, "R." At 510, the absorbance data may be adjusted such as using multiplicative scatter correction, such as to reduce or eliminate wavelength-dependent scatter. At 515, derivative values for the adjusted data from 510 may be estimated, such as using a finite-difference technique, such as to establish a vector indicative of a first derivative of the adjusted data from 510. At 520, a vector defining regression coefficients (e.g., a model profile) may be applied to the estimated derivative values to obtain a scalar value indicative of the characteristic being assessed. As mentioned above, the model profile may represent a set of coefficients determined using a partial least squares (PLS) regression technique.

Figure 6:
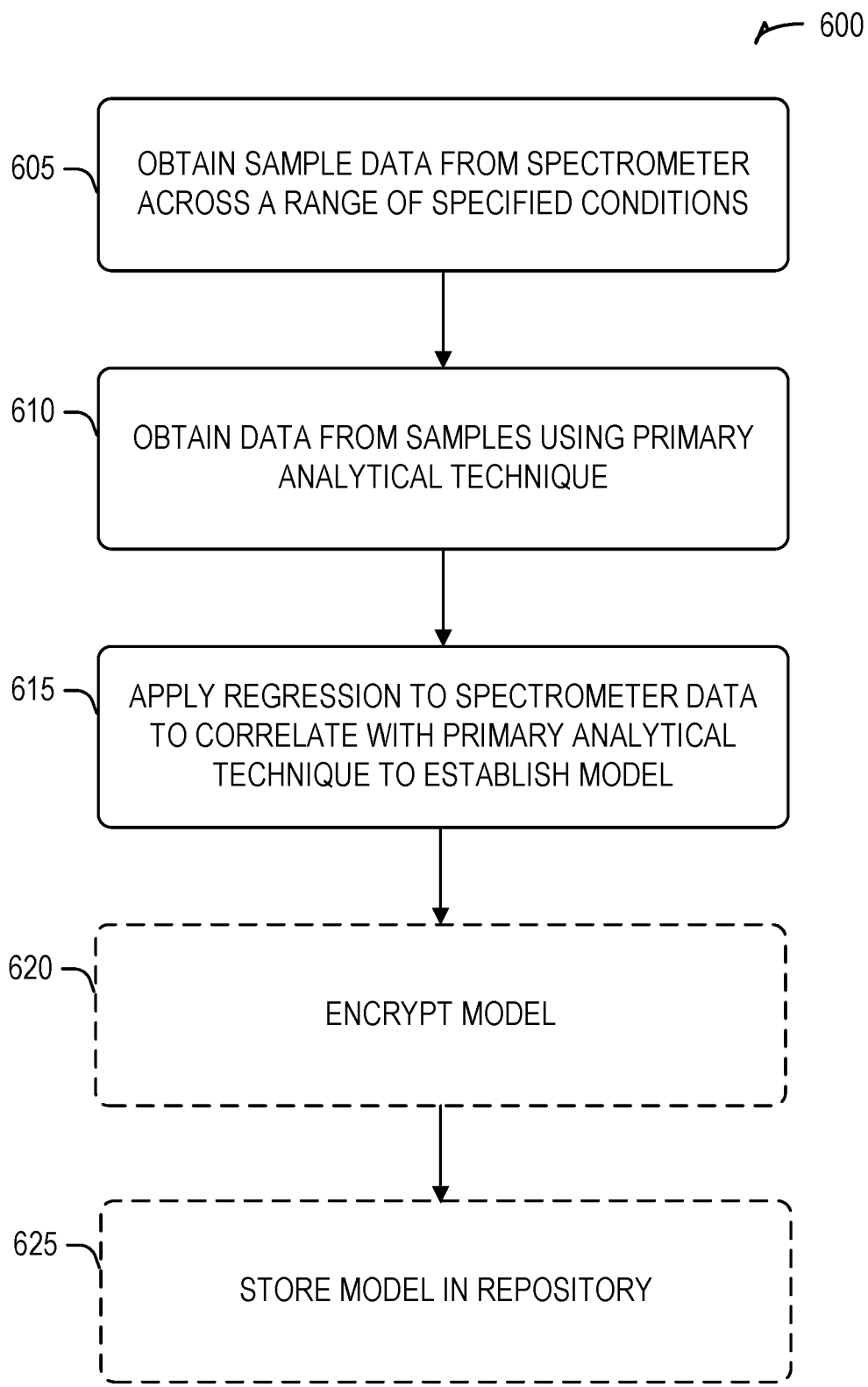
FIG. 6 illustrates generally an example comprising a technique, such as an automated method, including establishing a model profile for use in transforming data obtained using spectroscopy to obtain a value indicative of a characteristic of edible oil.

FIG. 6 illustrates generally an example comprising a technique 600, such as an automated method, including establishing a model profile for use in transforming data obtained using spectroscopy to obtain a value indicative of a characteristic of edible oil. At 605, data may be obtained from a "field" spectrometer (e.g., a low-cost hand-held spectrometer of the type to be used in the field or its equivalent) across a range of specified sample conditions. For example, such conditions may include a range of edible oil temperatures, a variety of oil types, a variety of oil states from new (e.g., fresh) to degraded (e.g., used and approaching or at a discard threshold). Other conditions may include the type of food being fried in the oil for which the model profile will be established (e.g., french-fried potatoes, breaded chicken, or egg rolls, as illustrative examples). At 610 data may be obtained from the same samples using a primary analytical technique or reference technique (e.g., a bench analytical technique performed according to a published standard, or obtained via a different instrument than the field spectrometer). For example, at 610, sampling may be replicated using the primary technique and correlated with the corresponding data obtained from the sample under similar conditions as were obtained at 605 with the field spectrometer (or its equivalent).

At 615, a regression may be applied to the spectrometer data to correlate it with the primary analytical technique (or another reference technique) to establish the model profile. For example, a partial least squares regression technique may be used, such as to establish a model profile comprising a vector of weights to be applied to data obtained from the spectrometer. In this manner, a regression-derived model may be established corresponding to (a) a desired oil characteristic to be assessed and (b) calibrated to suppress one or more of bias or error associated with sample variations such as oil type or temperature dependence. Optionally, at 620, the model profile may be encrypted, such as to prevent unauthorized use of the model profile or to inhibit the model profile from being duplicated or otherwise used in systems in which the model profile has not been validated. Various techniques can be used to securely store, securely transmit, securely decode, or securely encode the model, or to validate that the model is authentic (e.g., using a hash and comparing a determined hash value from a model instance to a stored hash value indicative of a valid or authentic model, and indicating whether the hash values match). At 625, the model profile may be stored in a repository, such as a centralized server or cloud-based facility. As mentioned in relation to other examples herein, the repository may implement permissions and a secure transaction facility to securely transfer the model profile (or related key information) or otherwise impose permissions on use of the model profile.

Figure 7:
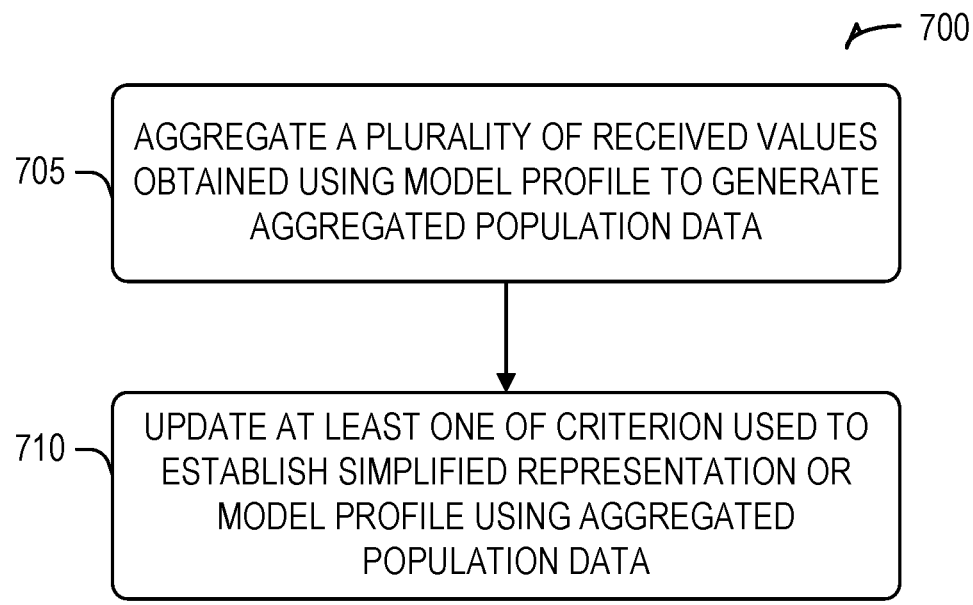
FIG. 7 illustrates generally an example comprising a technique, such as an automated method, including updating a model profile or a criterion used to establish a simplified representation of a characteristic of an edible oil using aggregated population data.

FIG. 7 illustrates generally an example comprising a technique 700, such as an automated method, including updating a model profile or a criterion used to establish a simplified representation of a characteristic of an edible oil using aggregated population data. For example, at 705, values of the edible oil characteristic may be received and aggregated, such as using a repository comprising a remote server or other resource. Aggregated population data may be generated. Such aggregated population data may reveal trends or other information that permit refinement or revision of the model profile or a criterion used to establish the simplified representation mentioned in relation to other examples herein. For example, at 710, the population data may be used to update at least one of a criterion used to establish the simplified representation or a model profile used for establishing the characteristic being assessed. As an illustrative example, if population data indicate that oil is being replaced or discarded well below a present "discard" threshold, then the discard threshold may be reduced to increase sensitivity. Thresholds used for binning (e.g., as shown illustratively in FIG. 9) may be established adaptively using one or more machine learning techniques, such as a deep convolutional neural network (DCNN) approach, a soft independent modeling of class analogies (SIMCA) approach, or using one or more other techniques. In such a manner, clusters of values of edible oil characteristics may be used to determine thresholds for a simplified representation (e.g., oil state) provided to a user. In another example, the aggregated population data may be correlated with subjective assessments of food quality (e.g., taste, texture/mouthfeel, or aroma, as illustrative examples) to determine weightings of edible oil characteristics having predictive value relating to food quality.

Figure 8:
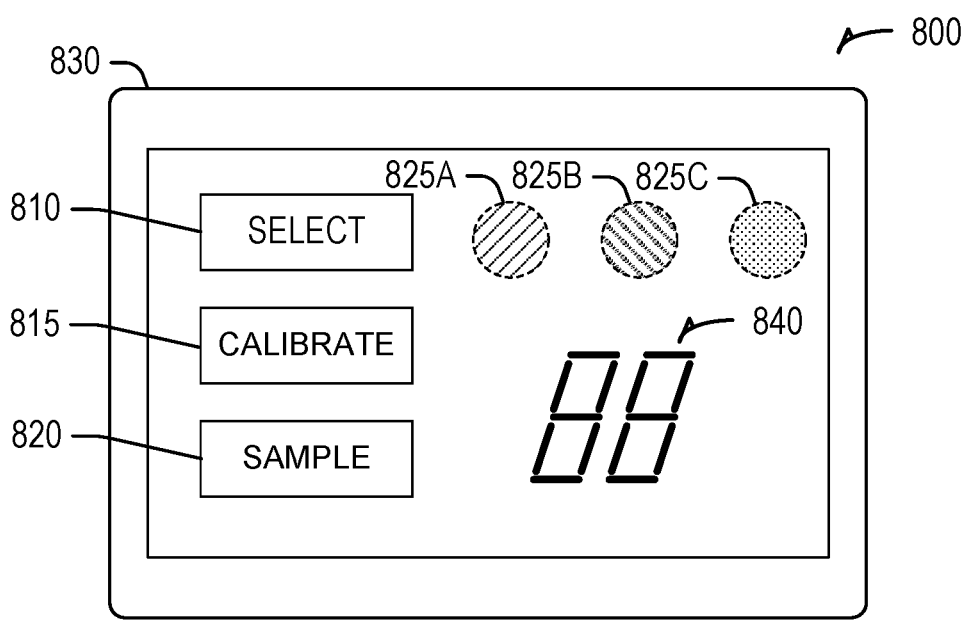
FIG. 8 illustrates generally an example comprising a user input and display, such as a touch-screen user interface, such as may be used to receive inputs to control a spectrometer or to present results, such as a simplified representation of a characteristic of an edible oiled being assessed using the spectrometer.

FIG. 8 illustrates generally an example 800 comprising a user input and display, such as a touch-screen user interface 830, such as may be used to receive inputs to control a spectrometer or to present results, such as a simplified representation of a characteristic of an edible oiled being assessed using the spectrometer. Such a user interface may be included as a portion of a spectrometer (such as the spectrometer 110 shown in FIG. 1), or a separate device in communication with the spectrometer, such as a mobile device or tablet. As an illustrative example, an input 810 may be used to receive an indication from the user that a particular model profile is to be selected, and a separate menu may show available model profiles authorized for use. Another input 815 may be used to receive an indication from the user that the spectrometer is to be calibrated. For example, the SCiO device mentioned elsewhere herein may be calibrated before each use, such as by coupling the SCiO device to a cover or base including a material having a known spectroscopic profile, and triggering a calibration. An input 820 may used to receive an indication from the user that a sample is to be initiated, such as to obtain reflectance data from an edible oil in situ.

As mentioned in relation to various examples herein, a model profile may be used to transform data obtained using the spectrometer to establish a value of a characteristic being assessed, such as TPM, FFA, color, polymer level. The value itself may be presented on the display of the touch-screen user interface 830 or a simplified representation may be presented. For example, the simplified representation may include a visual indication that the oil is at an intermediate state between fresh and a state where replacement is recommended, such as via a "traffic light" (green/yellow/red) style representation having three indicators 825A, 825B, or 825C representing oil states. Such states may be defined in a variety of manners, such as including a first state corresponding to "OK" or "Fresh," an intermediate state such as "Used" or "Filter," indicative that the oil is not yet at the discard point, and a third state indicative that the oil should be discarded.

The interface of the example 800 of FIG. 8 shows user inputs unified with a display for presentation of results, but these elements could also be separate. For example, the inputs may be provided by soft-keys aligned with a display, or by a separate keypad or input (e.g., switches, knobs, etc.). The display may include a bit-field display or other display (e.g., an LED or liquid-crystal display having pre-defined display elements, such as a numerical indicator 840 having seven-segment digits or other arrangement or indicators 825A, 825B, 825C comprising LED lamps). As an illustrative example, a unitless scale may be shown, such as a simplified numerical scale having values from one to five, or one to ten, such as having higher values to indicate higher oil quality (e.g., with five indicating new or fresh oil on a five-point scale or ten indicating new or fresh oil on a ten point scale).

Figure 9:
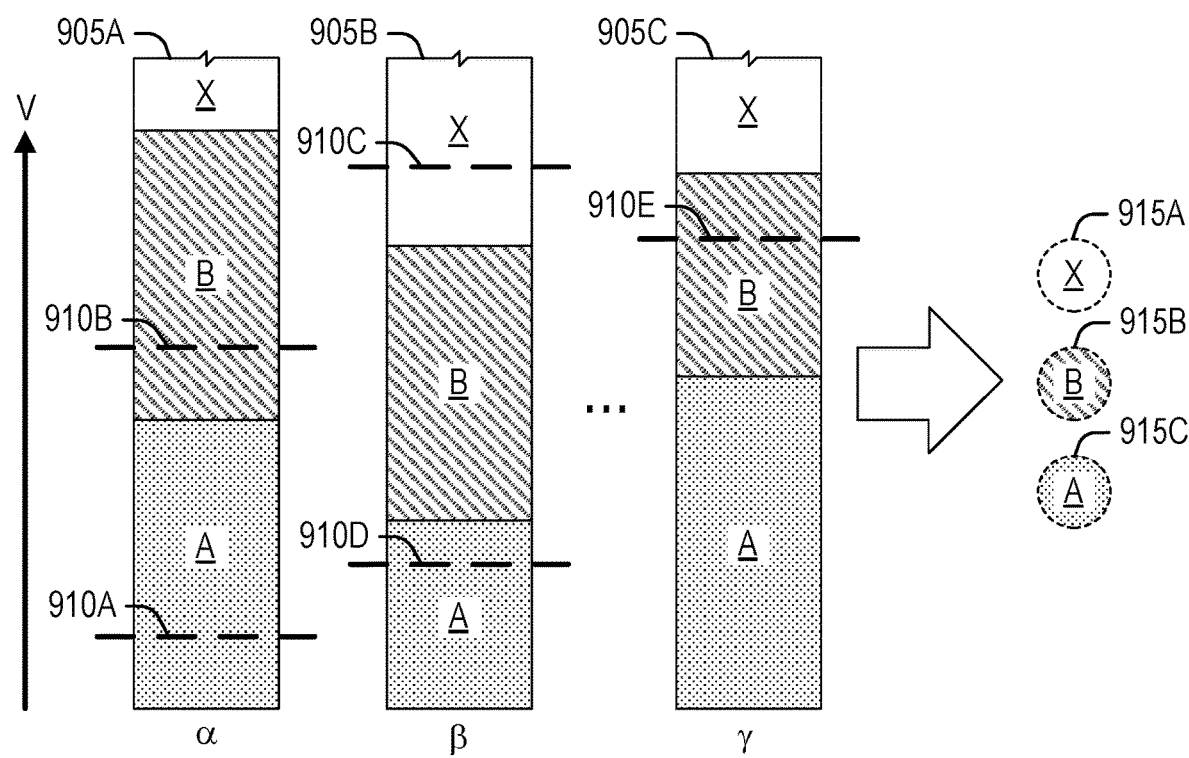
FIG. 9 illustrates generally illustrative examples of techniques for establishing a simplified representation of a characteristic of an edible oiled being assessed using the spectrometer, such as by evaluating criteria applied to respective values obtained using respective model profiles.

FIG. 9 illustrates generally illustrative examples of techniques for establishing a simplified representation of a characteristic of an edible oiled being assessed using the spectrometer, such as by evaluating criteria 905A, 905B, or 905C, applied to respective values obtained using respective model profiles. In an illustrative example, a characteristic being assessed (such as one of $\alpha$, $\beta$, or $\gamma$ as shown illustratively in FIG. 9) may include thresholds defining regions or "bins" A, B, and X respectively corresponding to different ranges of values, as shown by the axis, V. The characteristics $\alpha$, $\beta$, or $\gamma$ may correspond to one of an FFA, TPM, a color metric, a polymer content, or a Testo® value, respectively, as illustrative examples. The thresholds defining the regions A, B, and X for each of α, β, or γ may be predetermined, or may be adjusted in an adaptive or dynamic matter such as according to aggregated population statistics or in relation to a detected or selected geographical locale of the spectrometer, as illustrative examples. In an illustrative example, a simplified representation of a value of an edible oil characteristic may include a "traffic light" style display as shown by the indicators 915A, 915B, and 915C. Use of separate indicators is illustrative, and a single indicator capable of changing color may be used, for example, such as an LED lamp, a feature on a bit-field display, or a display backlight color. In an example, a single characteristic, α, may be used to establish the simplified representation according to the first criterion 905A. For example, if reflectance data is obtained, transformed, and the model profile corresponding to characteristic a is applied, resulting in a value 910A within the region A, then the first indicator 915C may be illuminated indicating that the edible oil is acceptable for further use.

If reflectance data from a later sample of the same oil reveals a value 910B within region B after applying the model profile corresponding to the parameter α, then the second indicator 915B may be illuminated to indicate that the edible oil is in an intermediate state, and so on. As described in relation to FIG. 3, a simplified representation may represent a unified representation of various criteria applied to multiple characteristics being assessed. For example, two or more characteristics selected from α, β, and γ may be applied jointly according to specified rules. For example, such rules may be expressed in terms of a Boolean "OR" (e.g., if any of α, β, and γ provides a value within the region B, then the result is illuminate the middle indicator 915B, or if any of α, β, and γ provides a value within the region X, then illuminate the third indicator 915A). This assumes that region A represents new or lightly used oil, region B represents an intermediate state, and X may represent a region where replacement (discard) is recommended. An illustrative example of a first rule set is included below in Table 1:

TABLE 1 an illustrative example of applying criteria 905A, 905B, 905C to establish a unified result, for different sampling outcomes.

| | α (905A) | β (905B) | γ (905C) | Overall Result |
|---|---|---|---|---|
| Sample Result | 910A | 910D | 910E | B (915B) |
| Sample Result | 910A | 910C | 910E | X (915A) |
| Sample Result | 910B | 910D | 910E | B (915B) |
| Sample Result | 910B | 910C | 910E | X (915A) |

Use of three bins to define each of the criteria 905A, 905B, or 905C to determine the simplified representation is illustrative. Other counts of bins may be used, such as a simple two-region approach (e.g., a "red light"/"green light" representation), or thresholds defining four regions (e.g., defining "new," "used," "filter," and "discard" regions, for example).

Figures 10A, 10B:
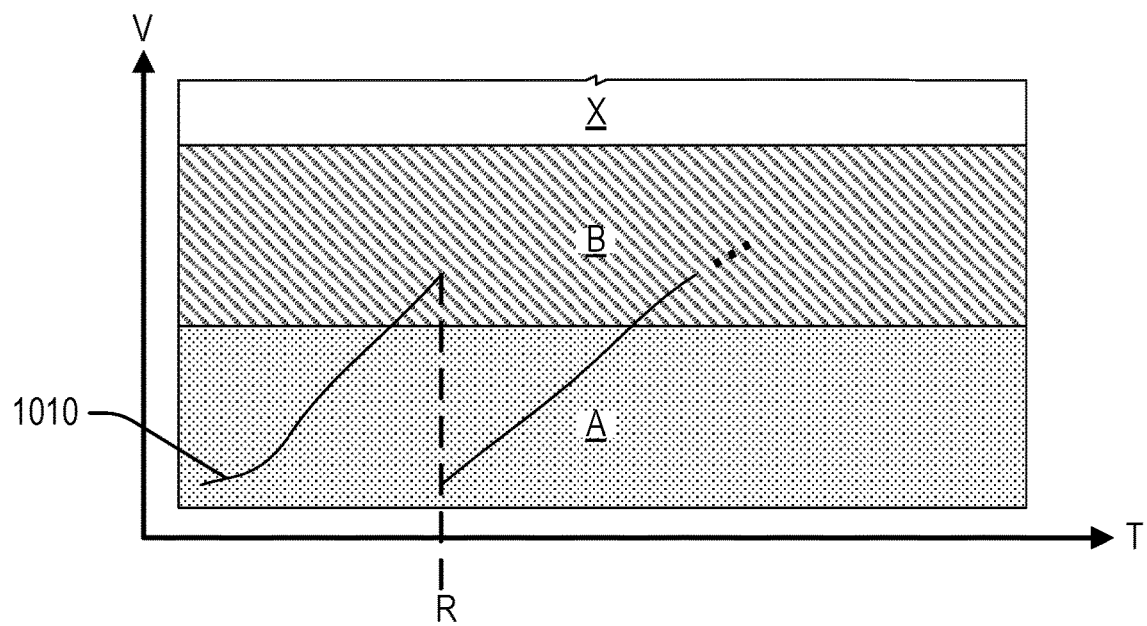
FIG. 10A illustrates generally an illustrative example of a report that may be generated using stored data obtained from a spectrometer to assess one or more characteristics of an edible oil.
FIG. 10B illustrates generally an illustrative example of a report providing a time-evolution of a characteristic of an edible oil using data obtained from a spectrometer.

FIG. 10A illustrates generally an illustrative example of a report that may be generated using stored data obtained from a spectrometer (such as in the context of the system 100 shown in FIG. 1) to assess one or more characteristics of an edible oil. In the illustrative example of FIG. 10A, a repository may store results obtained from a single site encompassing multiple fryer units, or multiple sites encompassing multiple fryer units. The report may include information suitable for tracing a specific spectrometer used for testing, along with identifying information relating to a site where the fryer units were tested. Values of edible oil characteristics being assessed with the spectrometer may be reported (as illustrated by columns α and β). If a simplified representation was established, such as mentioned in relation to other examples herein, the simplified representation may also be reported (e.g., shown in the RESULT column), such as illustrating an indication provided to a user of the spectrometer at the time the edible oil was sampled. As mentioned above in relation to FIG. 8 and other examples, the simplified representation may be established using one or more criteria applied to the edible oil characteristic being sampled, such as using fixed or adjustable threshold defining two or more "bins."

FIG. 10B illustrates generally an illustrative example of a report providing a time-evolution of a characteristic of an edible oil using data obtained from a spectrometer. In the illustrative example of FIG. 10B, a graphical representation of time-evolution may be plotted, such as generated using data stored in a repository and obtained from spectrometer (e.g., in the context of the system 100 shown in FIG. 1). In FIG. 10B, a value 1010 of the characteristic being assessed (e.g., TPM, FFA, a color metric, or another characteristic) is plotted over time and treatment (e.g., filtering) or replacement of the oil (such as denoted at time, "R") is visible. Thresholds or areas defining regions such as A, B, and X may be overlaid to indicate how the value 1010 would relate to a simplified representation of oil status presented to a user, such as to demonstrate continuous compliance with a regulatory or quality limit corresponding to a threshold (such as a threshold defined by a boundary between regions denoted "B" and "X" in FIG. 10B).

Experimentally-Obtained Results

The results shown in FIG. 11, FIG. 12, FIG. 13, FIG. 14, and FIG. 15 were obtained using a SCiO device mechanically anchored above a respective oil sample. The oil sample was housed in a heat-safe container with an open lid to provide an optical path length of approximately 1.5 inches. Oil samples were placed in an oven, the oven heated to 180 degrees Celsius, until the oil sample temperature reached approximately 180° C. Triplicate samples were obtained over a duration of about 25 seconds total. The reflectance data obtained from the SCiO device was transformed in accordance with the technique 500 described in relation to FIG. 5. A partial least squares (PLS) regression technique was performed to determine a regression vector by comparing sampled results obtained using the SCiO device to results obtained using a primary standard or other reference. The resulting regression vectors may be used as respective model profiles as mentioned in relation to other examples described herein to provide a calibrated scalar value of the characteristic being assessed. In each of FIG. 11, FIG. 12, FIG. 13, FIG. 14, and FIG. 15, the regression statistics are shown along with a relationship between values obtained using the SCiO device (after applying the regression to transform the reflectance data).

Figure 11:
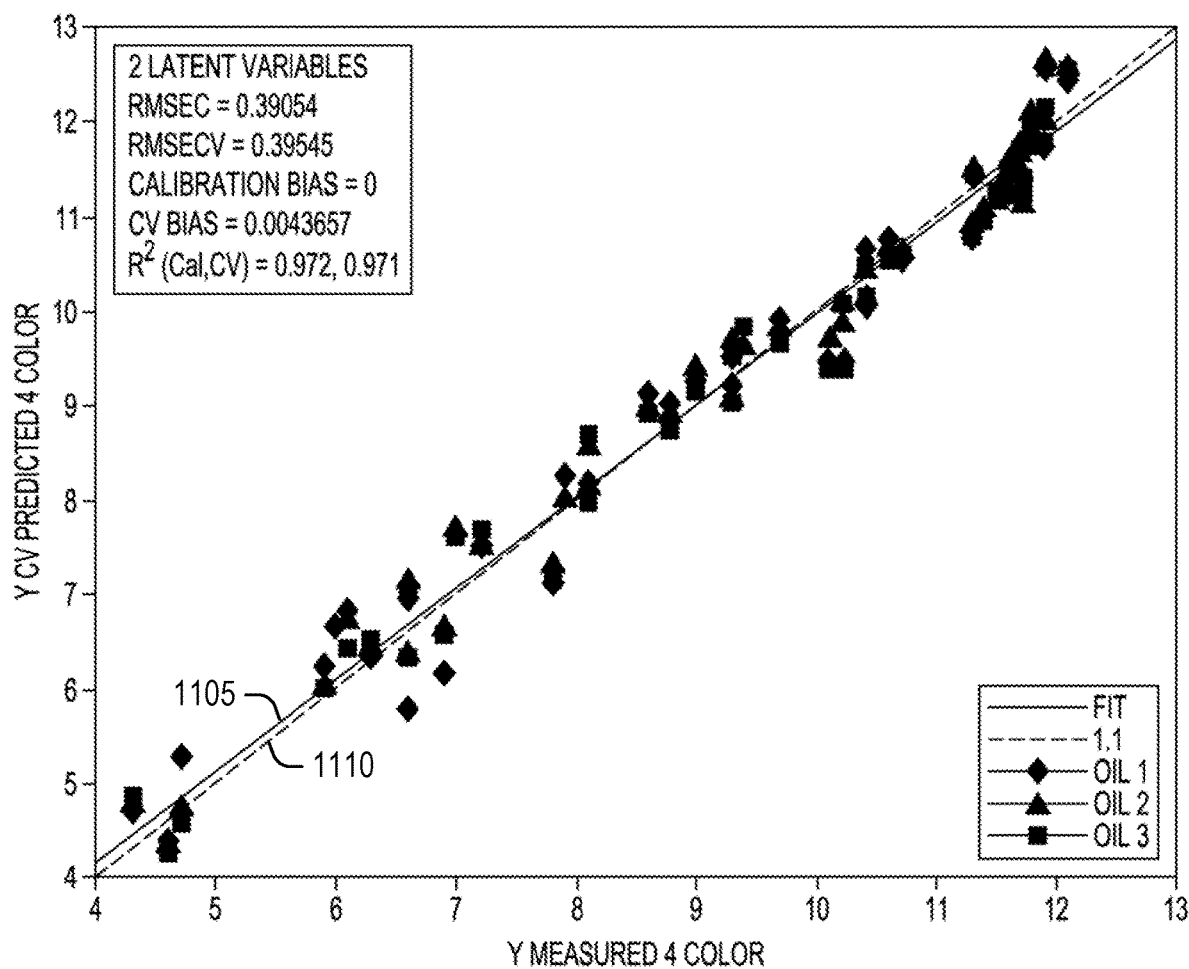
FIG. 11 illustrates generally an illustrative example of experimentally-obtained results including an estimated color parameter value obtained by transforming spectroscopic data, plotted versus corresponding measurements of the color parameter using a primary technique.

FIG. 11 illustrates generally an illustrative example of experimentally-obtained results including an estimated color parameter value obtained by transforming spectroscopic data, plotted versus corresponding measurements of the color parameter using a primary technique. A regression line 1105 is shown overlaid on a 1:1 line 1110, for comparison.

Triplicate measurements for each of a high oleic canola oil, a soybean oil, and a blend (canola oil, corn oil, and soybean oil) are shown.

Figure 12:
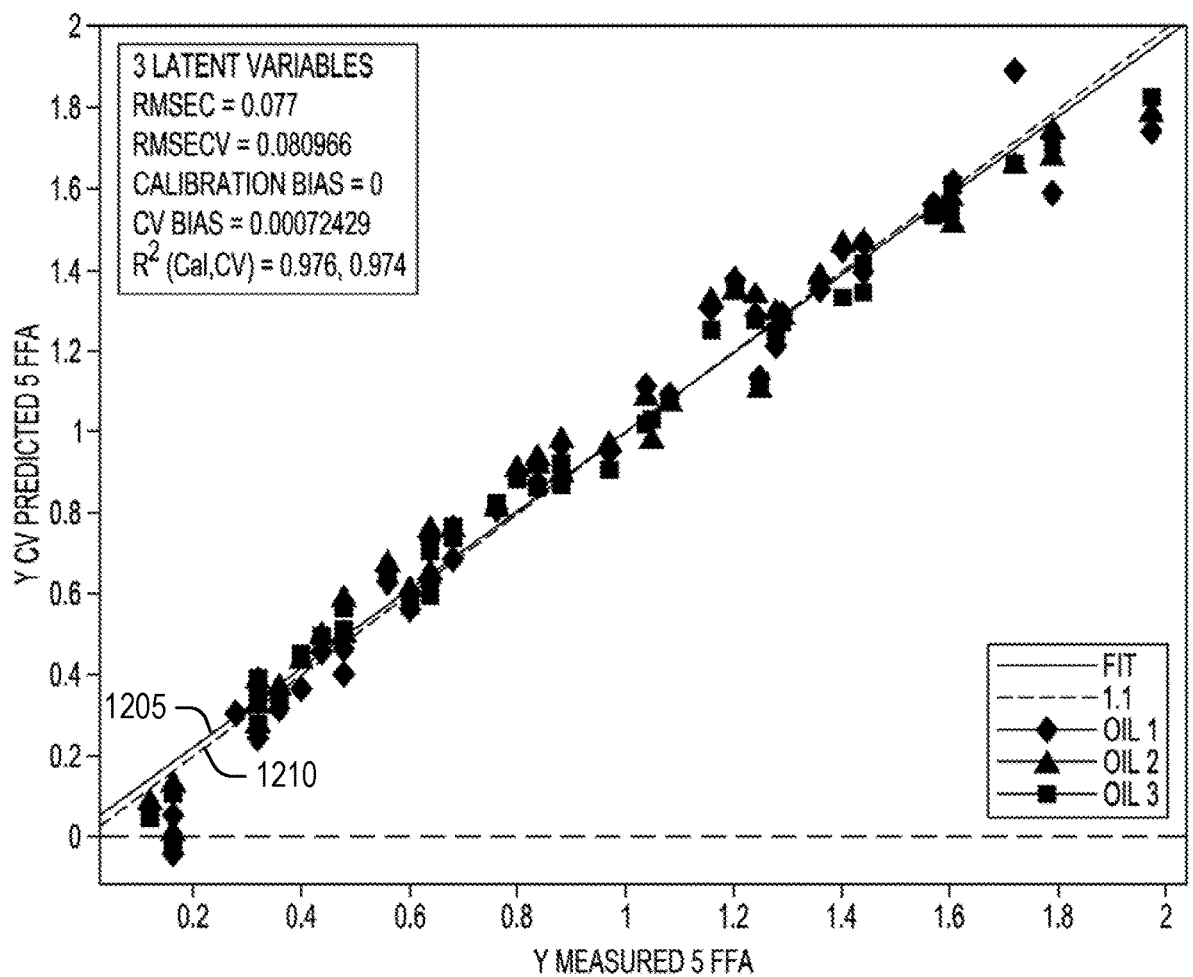
FIG. 12 illustrates generally an illustrative example of experimentally-obtained results including an estimated free fatty acid (FFA) value obtained by transforming spectroscopic data, plotted versus corresponding measurements of the FFA value using a primary technique.

FIG. 12 illustrates generally an illustrative example of experimentally-obtained results including an estimated free fatty acid (FFA) value obtained by transforming spectroscopic data, plotted versus corresponding measurements of the FFA value using a primary technique. A regression line 1205 is shown overlaid on a 1:1 line 1210, for comparison. Triplicate measurements for each of a high oleic canola oil, a soybean oil, and a blend (canola oil, corn oil, and soybean oil) are shown.

Figure 13:
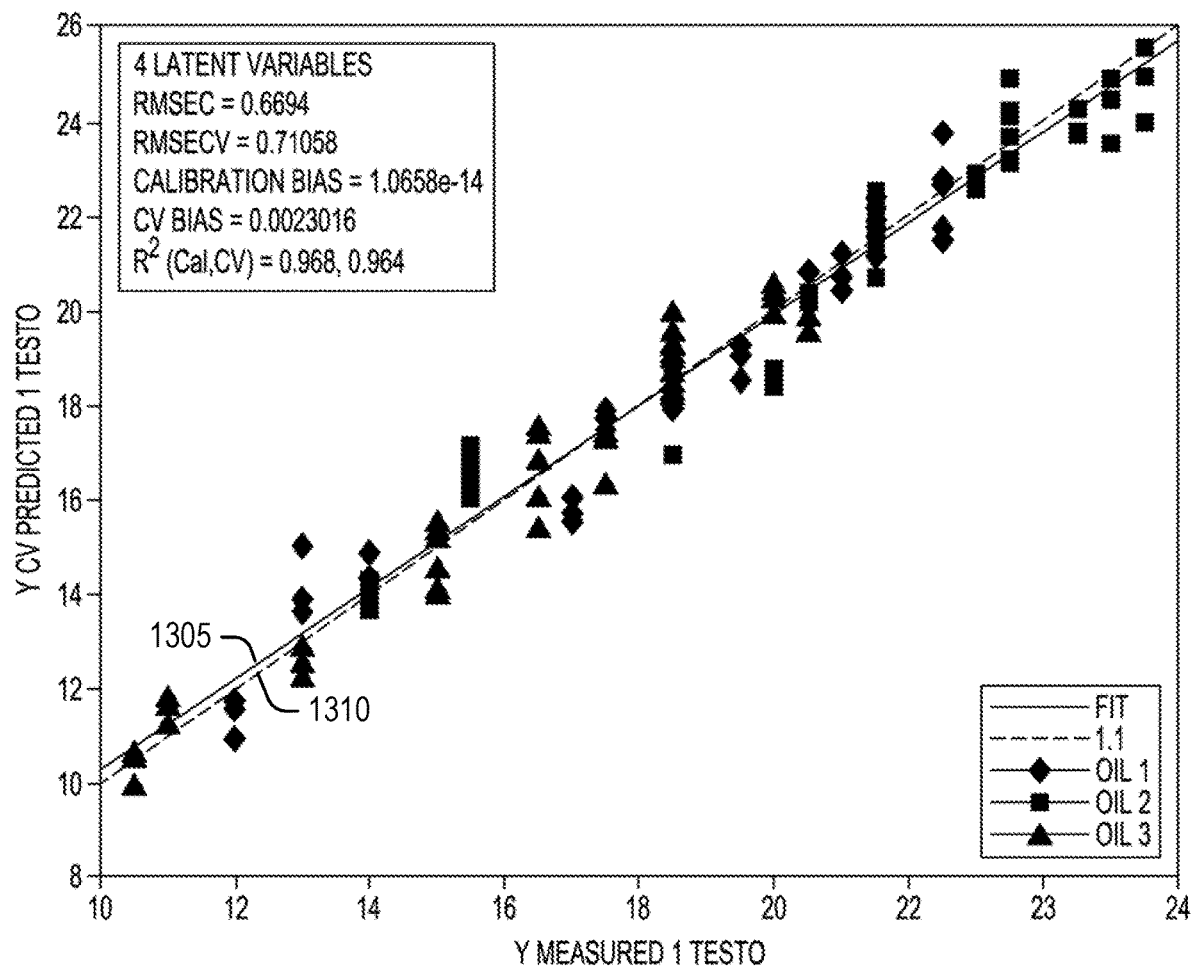
FIG. 13 illustrates generally an illustrative example of experimentally-obtained results including an estimated Testo® instrument value obtained by transforming spectroscopic data, plotted versus corresponding measurements of the Testo® instrument value using a Testo® instrument.

FIG. 13 illustrates generally an illustrative example of experimentally-obtained results including an estimated Testo® instrument value obtained by transforming spectroscopic data, plotted versus corresponding measurements of the Testo® instrument value using a Testo® instrument. A regression line 1305 is shown overlaid on a 1:1 line 1310, for comparison. Triplicate measurements for each of a high oleic canola oil, a soybean oil, and a blend (canola oil, corn oil, and soybean oil) are shown.

Figure 14:
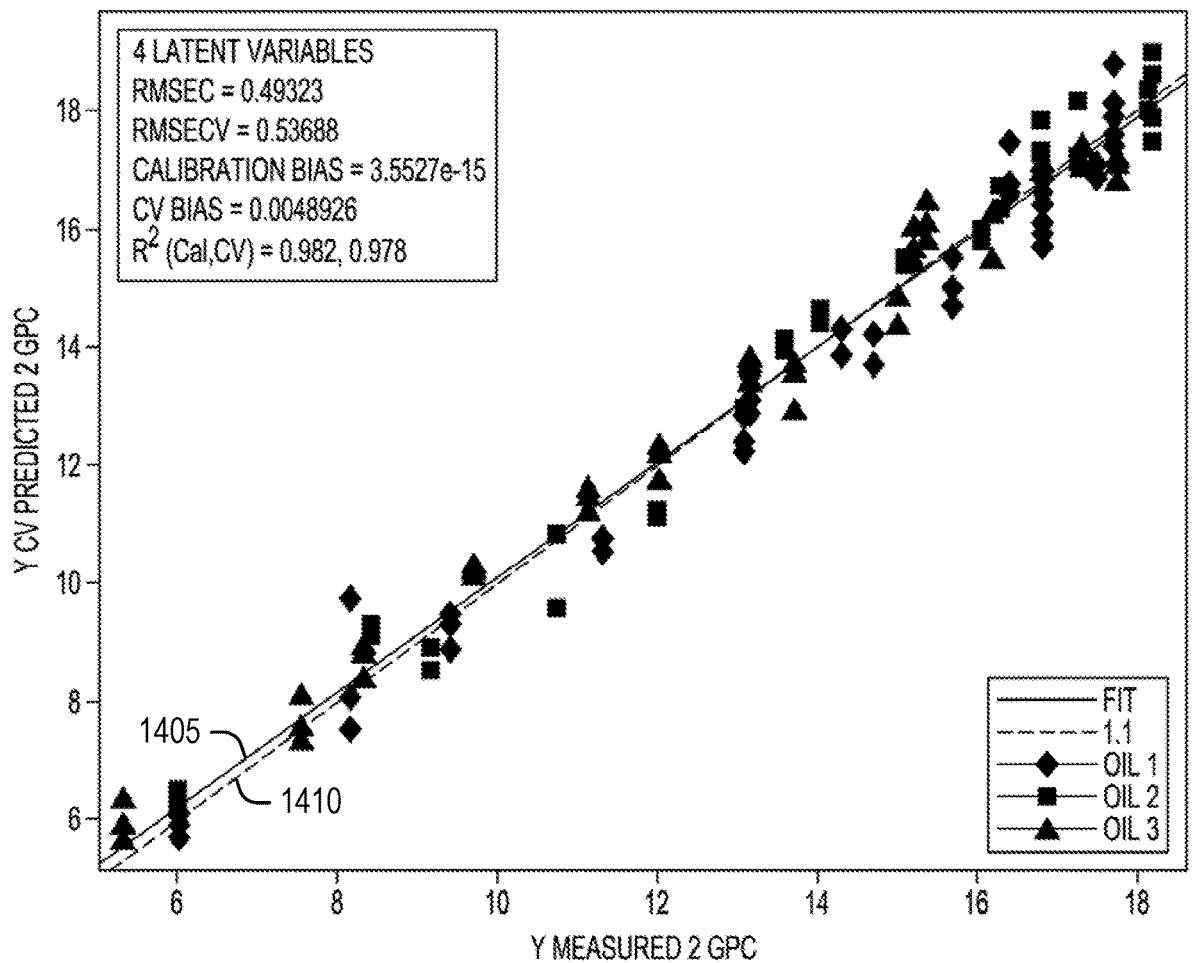
FIG. 14 illustrates generally an illustrative example of experimentally-obtained results including an estimated TPM value obtained by transforming spectroscopic data, plotted versus corresponding measurements of the TPM value using a gel permeation chromatography (GPC) instrument.

FIG. 14 illustrates generally an illustrative example of experimentally-obtained results including an estimated TPM value obtained by transforming spectroscopic data, plotted versus corresponding measurements of the TPM value using a GPC. A regression line 1405 is shown overlaid on a 1:1 line 1410, for comparison. Triplicate measurements for each of a high oleic canola oil, a soybean oil, and a blend (canola oil, corn oil, and soybean oil) are shown.

Figure 15:
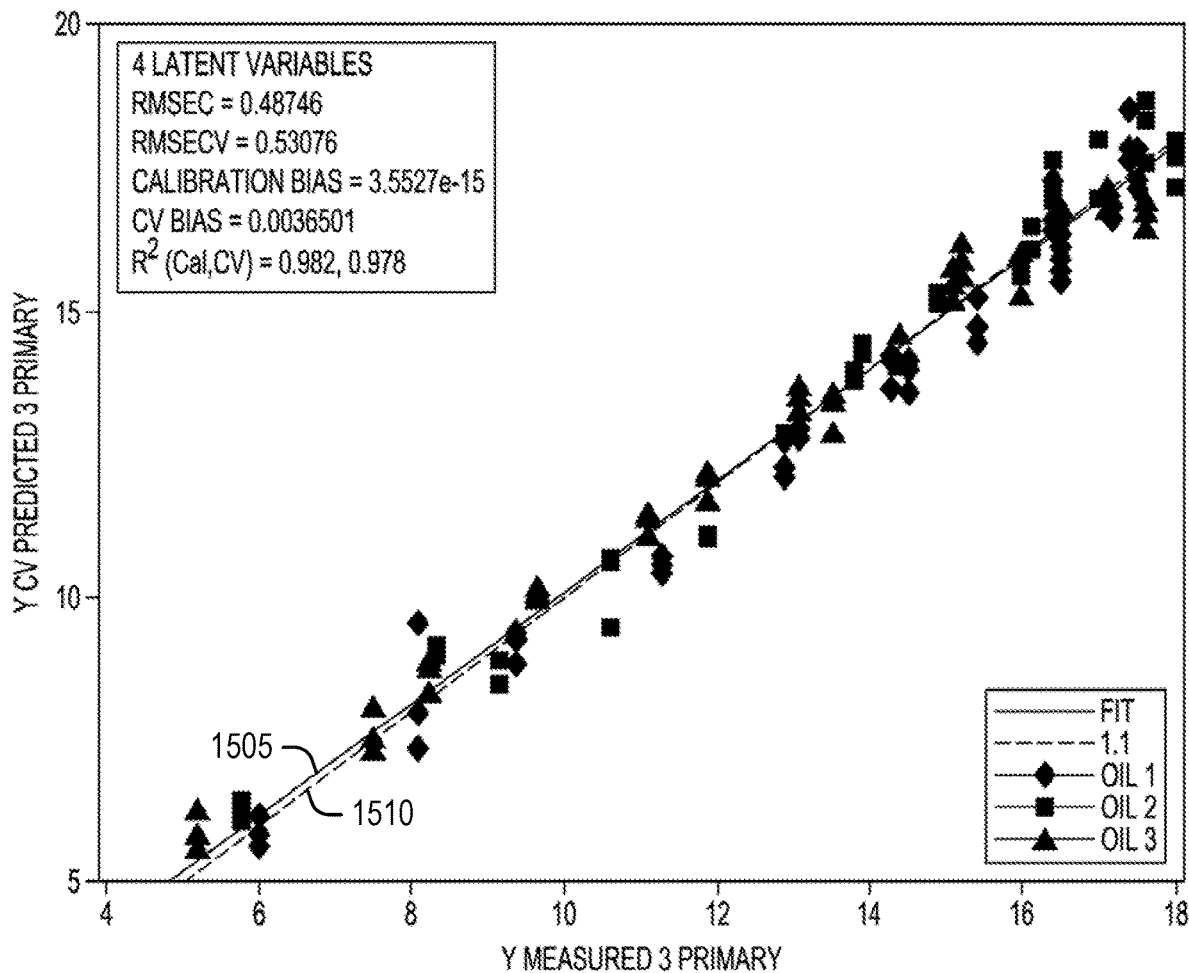
FIG. 15 illustrates generally an illustrative example of experimentally-obtained results including an estimated Total Polar Material (TPM) value obtained by transforming spectroscopic data, plotted versus corresponding measurements of the TPM value performed according to American Oil Chemist's Society (AOCS) Cd 20-91.

FIG. 15 illustrates generally an illustrative example of experimentally-obtained results including an estimated Total Polar Material (TPM) value obtained by transforming spectroscopic data, plotted versus corresponding measurements of the TPM value performed according to American Oil Chemist's Society (AOCS) Cd 20-91.

A regression line 1505 is shown overlaid on a 1:1 line 1510, for comparison. Triplicate measurements for each of a high oleic canola oil, a soybean oil, and a blend (canola oil, corn oil, and soybean oil) are shown.

Figure 16:
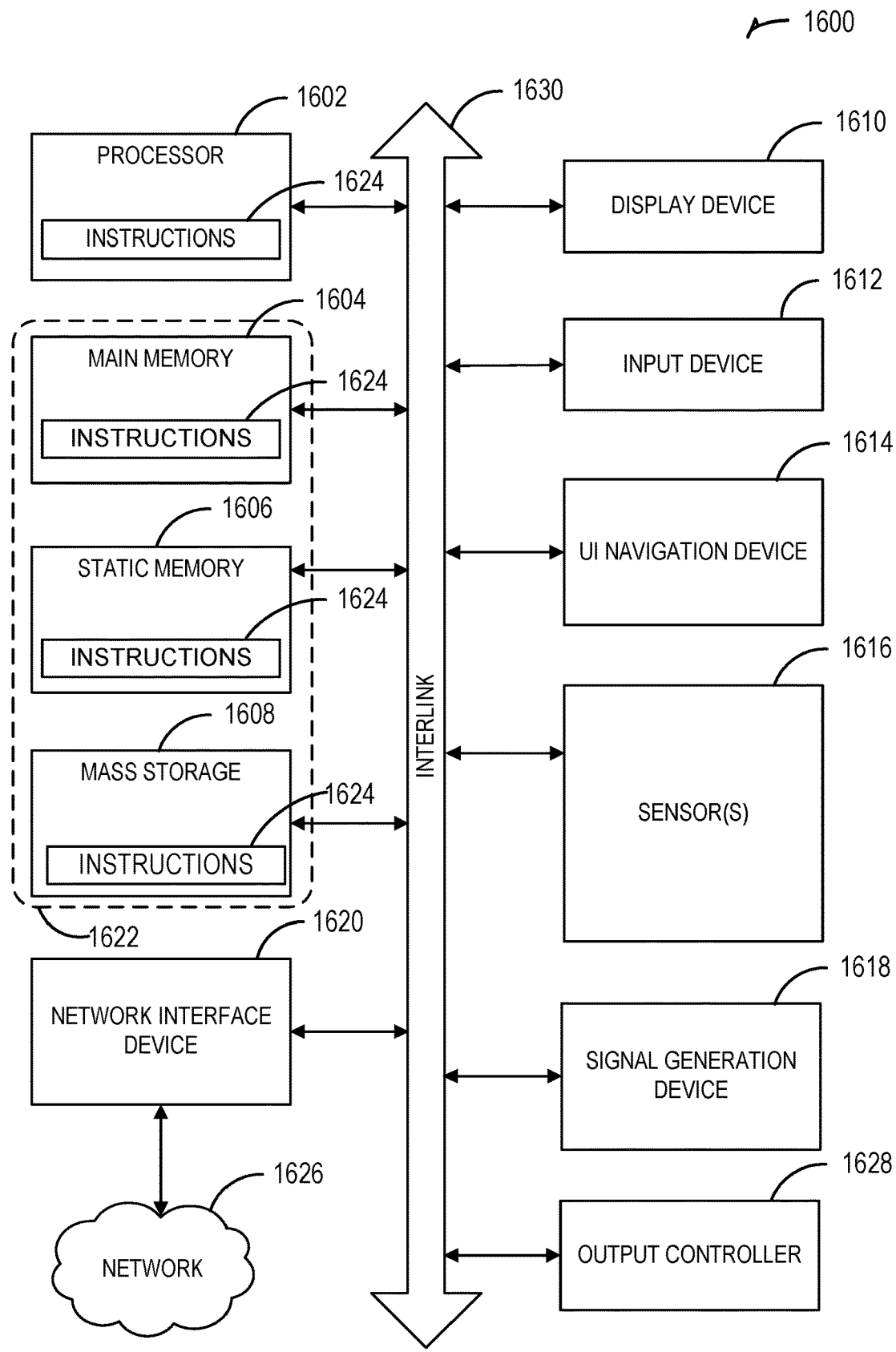
FIG. 16 illustrates a block diagram of an example comprising a machine upon which any one or more of the techniques (e.g., methodologies) discussed herein may be performed.

FIG. 16 illustrates a block diagram of an example comprising a machine 1600 upon which any one or more of the techniques (e.g., methodologies) discussed herein may be performed. The machine 1600 may be included as a portion of elements shown in the system 100 of FIG. 1. In various examples, the machine 1600 may operate as a standalone device or may be connected (e.g., networked) to other machines. In a networked deployment, the machine 1600 may operate in the capacity of a server machine, a client machine, or both in server-client network environments. In an example, the machine 1600 may act as a peer machine in peer-to-peer (P2P) (or other distributed) network environment. The machine 1600 may be a personal computer (PC), a tablet device, a personal digital assistant (PDA), a mobile telephone, a web appliance, a network router, switch or bridge, a portable (e.g., hand-held) spectrometer such as including a microprocessor or microcontroller, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. "Circuitry" refers generally a collection of circuits implemented in tangible entities that include hardware (e.g., simple circuits, gates, logic elements, etc.). Circuitry membership may be flexible over time and underlying hardware variability. Circuitries include members that may, alone or in combination, perform specified operations when operating. In an example, hardware of the circuitry may be immutably designed to carry out a specific operation (e.g., hardwired). In an example, the hardware comprising the circuitry may include variably connected physical components (e.g., execution units, transistors, simple circuits, etc.) including a computer readable medium physically modified (e.g., magnetically, electrically, such as via a change in physical state or transformation of another physical characteristic, etc.) to encode instructions of the specific operation.

In connecting the physical components, the underlying electrical properties of a hardware constituent may be changed, for example, from an insulating characteristic to a conductive characteristic or vice versa. The instructions enable embedded hardware (e.g., the execution units or a loading mechanism) to create members of the circuitry in hardware via the variable connections to carry out portions of the specific operation when in operation. Accordingly, the computer readable medium is communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time.

Machine (e.g., computer system) 1600 may include a hardware processor 1602 (e.g., a central processing unit (CPU), a graphics processing unit (GPU), a hardware processor core, or any combination thereof), a main memory 1604 and a static memory 1606, some or all of which may communicate with each other via an interlink (e.g., bus) 1608. The machine 1600 may further include a display unit 1610, an alphanumeric input device 1612 (e.g., a keyboard), and a user interface (UI) navigation device 1614 (e.g., a mouse). In an example, the display unit 1610, input device 1612 and UI navigation device 1614 may be a touch screen display. The machine 1600 may additionally include a storage device (e.g., drive unit) 1616, a signal generation device 1618 (e.g., a speaker), a network interface device 1620, and one or more sensors 1621, such as a global positioning system (GPS) sensor, compass, accelerometer, or other sensor. The machine 1600 may include an output controller 1628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1616 may include a machine readable medium 1622 on which is stored one or more sets of data structures or instructions 1624 (e.g., software) embodying or utilized by any one or more of the techniques or functions described herein. The instructions 1624 may also reside, completely or at least partially, within the main memory 1604, within static memory 1606, or within the hardware processor 1602 during execution thereof by the machine 1600. In an example, one or any combination of the hardware processor 1602, the main memory 1604, the static memory 1606, or the storage device 1616 may constitute machine readable media.

While the machine readable medium 1622 is illustrated as a single medium, the term "machine readable medium" may include a single medium or multiple media (e.g., a centralized or distributed database, and/or associated caches and servers) configured to store the one or more instructions 1624.

The term "machine readable medium" may include any medium that is capable of storing, encoding, or carrying instructions for execution by the machine 1600 and that cause the machine 1600 to perform any one or more of the techniques of the present disclosure, or that is capable of storing, encoding or carrying data structures used by or associated with such instructions. Non-limiting machine readable medium examples may include solid-state memories, and optical and magnetic media. Accordingly, machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic or other phase-change or state-change memory circuits; magnetic disks, such as internal hard disks and removable disks; magneto-optical disks; and CD-ROM and DVD-ROM disks.

The instructions 1624 may further be transmitted or received over a communications network 1626 using a transmission medium via the network interface device 1620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks such as conforming to one or more standards such as a 4G standard or Long Term Evolution (LTE)), Plain Old Telephone (POTS) networks, and wireless data networks (e.g., Institute of Electrical and Electronics Engineers (IEEE) 802.11 family of standards known as Wi-Fi®, IEEE 802.15.4 family of standards, peer-to-peer (P2P) networks, among others. In an example, the network interface device 1620 may include one or more physical jacks (e.g., Ethernet, coaxial, or phone jacks) or one or more antennas to connect to the communications network 1626. In an example, the network interface device 1620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1600, and includes digital or analog communications signals or other intangible medium to facilitate communication of such software.

Various Notes

Example 1 can include or use subject matter (such as an apparatus, a method, a means for performing acts, or a device readable medium including instructions that, when performed by the device, can cause the device to perform acts), such as can include an automated method for spectroscopic evaluation of a characteristic of edible oil, the method comprising: using a spectrometer, optically obtaining reflectance data from the edible oil in situ in a frying apparatus housing the edible oil, the reflectance data corresponding to a specified range of infra-red wavelengths, securely obtaining a model profile corresponding to the characteristic being assessed, transforming the reflectance data using the model profile to generate a value corresponding to the characteristic, and applying a criterion to the value to establish a simplified representation of the characteristic for presentation to a user for assessment of oil quality.

In Example 2, the subject matter of Example 1 optionally includes transmitting the value to another device for at least one of presentation or storage.

In Example 3, the subject matter of any of Example 1 or Example 2 optionally includes securely obtaining two or more model profiles corresponding to respective different characteristic being assessed, transforming the reflectance data using the two or more model profiles to generate respective values corresponding to the respective different characteristics, and applying respective criteria to the values to establish the simplified representation.

In Example 4, the subject matter of Example 3 optionally includes that the simplified representation represents a predictive assessment of a quality of food prepared using the edible oil.

In Example 5, the subject matter of any of Example 1 through Example 3 optionally includes aggregating a plurality of received values obtained using the model profile to generate aggregated population data, and updating at least one of the criterion or the model profile using information extracted from the aggregated population.

In Example 6, the subject matter of any of Example 1 through Example 5 optionally includes that the criterion comprises a threshold, applying the criterion comprises comparing the value to the threshold; and that the simplified representation is determined in response to the comparison.

In Example 7, the subject matter of any of Example 1 through Example 6 optionally includes that the simplified representation comprises a visual indication to the user, representative of a status of the oil.

In Example 8, the subject matter of Example 7 optionally includes that the criterion includes assigning the value to a bin amongst a plurality of bins defined by different ranges of values of the characteristic and wherein the simplified representation corresponds to the assigned bin.

In Example 9, the subject matter of any of Example 1 through Example 8 optionally includes that the simplified representation is established using values obtained by applying a plurality of model profiles corresponding to different characteristics to the obtained reflectance data.

In Example 10, the subject matter of any of Example 1 through Example 9 optionally includes that the securely obtaining the model profile comprises receiving a representation of the model profile from a repository in response to validation that the user is authorized to apply the model profile for transforming the reflectance data.

In Example 11, the subject matter of Example 10 optionally includes that the model profile is accessed using a key, the key provided in response to validation that the user is authorized to apply the model profile for transforming the reflectance data.

In Example 12, the subject matter of any of Example 10 through Example 11 optionally includes that the repository comprises a plurality of model profiles corresponding to different respective characteristics.

In Example 13, the subject matter of Example 12 optionally includes that the the different respective characteristics include at least one of a free fatty acid (FFA) value, a Gardner color unit, or a total polar material (TPM) level.

In Example 14, the subject matter of any of Example 1 through Example 13 optionally includes receiving a selection of a characteristic to be assessed, from the user, where the obtained model profile corresponds to the selected characteristic.

In Example 15, the subject matter of any of Example 1 through Example 14 optionally includes that the securely obtaining the model profile comprises receiving a representation of the model profile from a repository, where the repository comprises a plurality of model profiles offering varying specified degrees of accuracy to provide different measurement performance levels.

In Example 16, the subject matter of any of Example 1 through Example 15 optionally includes that the securely obtaining the model profile comprises receiving a representation of the model profile from a repository, where the repository comprises a plurality of model profiles corresponding to different respective types of oil.

In Example 17, the subject matter of any of Example 1 through Example 16 optionally includes that the model profile is universal to at least two different respective types of oil.

In Example 18, the subject matter of Example 17 optionally includes that the at least two different respective types of oil include at least two of canola oil, soybean oil, corn oil, or combinations thereof.

In Example 19, the subject matter of any of Example 1 through Example 18 optionally includes that the model profile is established to provide the assessment across a specified range of temperatures without requiring a measurement of an oil temperature or entry of an oil temperature by a user.

In Example 20, the subject matter of any of Example 1 through Example 19 optionally includes that the model profile comprises a set of regression coefficients.

In Example 21, the subject matter of Example 20 optionally includes that the transforming the reflectance data comprises converting the reflectance data into absorbance data, adjusting the absorbance data to account for wavelength-dependent scatter, determining respective derivative values of the adjusted absorbance data corresponding to discrete wavelength values within the specified range of wavelengths, and multiplying a vector defining the regression coefficients by the derivative values to obtain the value indicative of the characteristic.

In Example 22, the subject matter of any of Example 1 through Example 21 optionally includes that the specified range of infra-red wavelengths includes a near-infrared (NIR) range of wavelengths from about 700 nanometers to about 1100 nanometers.

In Example 23, the subject matter of any of Example 1 through Example 20 optionally includes that the obtaining a model profile corresponding to the characteristic being assessed, transforming the reflectance data using the model profile to generate a value corresponding to the characteristic and applying a criterion to the value to provide a representation of the characteristic for presentation to a user are performed using a second device communicatively coupled to the spectrometer.

In Example 24, the subject matter of Example 23 optionally includes that the second device is located nearby the spectrometer and is wirelessly communicatively coupled to the spectrometer.

In Example 25, the subject matter of Example 23 optionally includes that the second device is located remotely with respect to the spectrometer, the second device communicatively coupled to the spectrometer through an intermediary device.

In Example 26, the subject matter of Example 25 optionally includes that the second device comprises a network-connected computing and storage system, where the intermediary device comprises a mobile device.

Example 27 can include or use subject matter (such as an apparatus, a method, a means for performing acts, or a device readable medium including instructions that, when performed by the device, can cause the device to perform acts), such as can include a system for spectroscopic evaluation of a characteristic of edible oil, the system comprising a spectrometer configured to emit light comprising a specified range of infra-red wavelengths, receive a reflection from edible oil in situ in a frying apparatus housing the edible oil, and establish reflectance data corresponding to the received reflection, the system comprising a processor circuit coupled to a memory circuit and communicatively coupled to the spectrometer, the processor circuit configured to securely obtain a model profile corresponding to the characteristic being assessed and to store the model profile in the memory circuit, transform the reflectance data obtained using the spectrometer, using the model profile to generate a value corresponding to the characteristic, and apply a criterion to the value to establish a simplified representation of the characteristic for presentation to a user for assessment of oil quality.

In Example 28, the subject matter of Example 27 optionally includes a repository configured to securely store a plurality of model profiles for retrieval, where the processor circuit is configured to securely obtain two or more model profiles from amongst the plurality of model profiles, the two or more model profiles corresponding to respective different characteristic being assessed, transform the reflectance data using the two or more model profiles to generate respective values corresponding to the respective different characteristics, and apply respective criteria to the values to establish the simplified representation.

In Example 29, the subject matter of Example 28 optionally includes that the simplified representation represents a predictive assessment of a quality of food prepared using the oil.

In Example 30, the subject matter of any of Example 27 through Example 29 optionally includes a repository configured to store and aggregate a plurality of received values of the characteristic established using the model profile to generate aggregated population data, where the processor circuit is configured to update at least one of the criterion or the model profile using information extracted from the aggregated population.

In Example 31, the subject matter of any of Example 27 through Example 30 optionally includes that the spectrometer comprises a display configured to present the simplified representation, the simplified representation comprising a visual indication to the user representative of a status of the oil.

In Example 32, the subject matter of Example 31 optionally includes that the simplified representation comprises a visual indication that the oil is at an intermediate state between fresh and a state where replacement is recommended.

In Example 33, the subject matter of any of Example 27 through Example 32 optionally includes that the processor circuit is configured to obtain the model profile by receiving an encrypted representation of the model profile from a repository.

In Example 34, the subject matter of Example 33 optionally includes that the processor circuit is configured to decrypt the representation of the model profile using a key, the key received in response to validation that the user is authorized to decrypt and apply the model profile for transforming the reflectance data.

In Example 35, the subject matter of any of Example 33 through Example 34 optionally includes a repository configured to store a plurality of model profiles.

In Example 36, the subject matter of Example 35 optionally includes that the repository includes a plurality of model profiles corresponding to different respective types of oil.

In Example 37, the subject matter of any of Example 35 through Example 36 optionally includes that the processor circuit is configured to receive a selection of a characteristic to be assessed, from the user, where the obtained model profile corresponds to the selected characteristic.

In Example 38, the subject matter of any of Example 35 through Example 37 optionally includes that the repository is configured to store a plurality of model profiles offering varying specified degrees of accuracy to provide different measurement performance levels.

In Example 39, the subject matter of any of Example 35 through Example 38 optionally includes that repository is configured to store a plurality of model profiles corresponding to different respective characteristics, where the different respective characteristics include at least one of a free fatty acid (FFA) value, a Gardner color unit, or a total polar material (TPM) level.

In Example 40, the subject matter of any of Example 27 through Example 39 optionally includes that the model profile is universal to at least two different respective types of oil.

In Example 41, the subject matter of Example 40 optionally includes that the the at least two different respective types of oil include at least two of canola oil, soybean oil, corn oil, or combinations thereof.

In Example 42, the subject matter of any of Example 27 through Example 41 optionally includes that the model profile is established to provide the assessment across a specified range of temperatures without requiring the processor circuit to control a measurement of an oil temperature or to receive an entry of an oil temperature by a user.

In Example 43, the subject matter of any of Example 27 through Example 42 optionally includes that the model profile comprises a set of regression coefficients.

In Example 44 the subject matter of any of Example 27 through Example 43 optionally includes that the processor circuit is configured to transform the reflectance data including converting the reflectance data into absorbance data, adjusting the absorbance data to account for wavelength-dependent scatter, determining respective derivative values of the adjusted absorbance data corresponding to discrete wavelength values within the specified range of wavelengths, and multiplying a vector defining the regression coefficients by the derivative values to obtain the value indicative of the characteristic.

In Example 45, the subject matter of any of Example 27 through Example 44 optionally includes that the specified range of infra-red wavelengths comprises a near-infrared (NIR) range of wavelengths from about 700 nanometers to about 1100 nanometers.

In Example 46, the subject matter of any of Example 27 through Example 45 optionally includes that the processor circuit and the memory circuit are housed in a second device communicatively coupled to the spectrometer.

In Example 47, the subject matter of Example 46 optionally includes that the second device is located nearby the spectrometer and is wirelessly communicatively coupled to the spectrometer.

In Example 48, the subject matter of Example 46 optionally includes that the second device is located remotely with respect to the spectrometer, the second device communicatively coupled to the spectrometer through an intermediary device.

In Example 49, the subject matter of Example 48 optionally includes that the second device comprises a network-connected computing and storage system, where the intermediary device comprises a mobile device.

In Example 50, the subject matter of any of Example 27 through Example 45 optionally includes that the processor circuit and the memory circuit are included as a portion of an assembly housing the spectrometer.

Example 51 can include or use subject matter (such as an apparatus, a method, a means for performing acts, or a device readable medium including instructions that, when performed by the device, can cause the device to perform acts), such as can include a system for spectroscopic evaluation of a characteristic of edible oil, the system comprising a spectrometer comprising a means for establishing reflectance data corresponding to a reflection received from edible oil in situ in a frying apparatus housing the edible oil, the reflectance data encompassing a specified range of infra-red wavelengths, a user interface means configured to receive a selection of the characteristic to be assessed, from the user, and a processing means coupled to the spectrometer and configured to securely obtain a model profile corresponding to the characteristic and to store the model profile in the memory circuit, transform the reflectance data obtained using the spectrometer, using the model profile to generate a value corresponding to the characteristic, and apply a criterion to the value to establish a simplified representation of the characteristic for presentation to a user for assessment of oil quality.

In Example 52, the subject matter of Example 51 optionally includes a repository configured to securely store a plurality of model profiles for retrieval, where the processing means is configured to securely obtain two or more model profiles from amongst the plurality of model profiles, the two or more model profiles corresponding to respective different characteristic being assessed, transform the reflectance data using the two or more model profiles to generate respective values corresponding to the respective different characteristics, and apply respective criteria to the values to establish the simplified representation for presentation to the user.

Each of the non-limiting aspects above can stand on its own, or can be combined in various permutations or combinations with one or more of the other aspects or other subject matter described in this document.

The above detailed description includes references to the accompanying drawings, which form a part of the detailed description. The drawings show, by way of illustration, specific embodiments in which the invention can be practiced. These embodiments are also referred to generally as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An automated method for spectroscopic evaluation of a characteristic of edible oil, the method comprising:
using a spectrometer, optically obtaining reflectance data from the edible oil in situ in a frying apparatus housing the edible oil, the reflectance data corresponding to a specified range of infra-red wavelengths;
obtaining a secure model profile corresponding to the characteristic being assessed using a processor circuit and storing the secure model profile in a memory circuit, wherein the characteristic comprises a free fatty acid (FFA) value;
transforming the reflectance data using the secure model profile to generate a value corresponding to the characteristic using the processor circuit; and
applying a criterion to the value to establish a simplified representation of the characteristic for presentation to a user for assessment of oil quality using the processor circuit.

2. The automated method of claim 1, comprising transmitting the value to another device for at least one of presentation or storage.

3. The automated method of claim 1, comprising obtaining two or more secure model profiles corresponding to respective different characteristics being assessed;
transforming the reflectance data using the two or more secure model profiles to generate respective values corresponding to the respective different characteristics; and
applying respective criteria to the values to establish the simplified representation;
wherein the characteristic further comprises at least a Gardner color unit, a total polar material (TPM) level, or combinations thereof.

4. The automated method of claim 1, comprising aggregating a plurality of received values obtained using the secure model profile to generate aggregated population data; and
updating at least one of the criterion or the secure model profile using information extracted from the aggregated population data.

5. The automated method of claim 1, wherein the criterion comprises a threshold;
wherein applying the criterion comprises comparing the value to the threshold; and
wherein the simplified representation is determined in response to the comparison.

6. The automated method of claim 1, wherein the simplified representation comprises a visual indication to the user, representative of a status of the edible oil.

7. The automated method of claim 6, wherein the simplified representation comprises a visual indication that the edible oil is at an intermediate state between fresh and a state where replacement is recommended; and
wherein the criterion includes assigning the value to a bin amongst a plurality of bins defined by different ranges of values of the characteristic and wherein the simplified representation corresponds to the assigned bin.

8. The automated method of claim 1, wherein the simplified representation is established using values obtained by applying a plurality of secure model profiles corresponding to different characteristics to the obtained reflectance data.

9. The automated method of claim 1, comprising receiving a selection of a characteristic to be assessed, from the user;
wherein the obtained secure model profile corresponds to the selected characteristic.

10. The automated method of claim 1, wherein obtaining the secure model profile comprises receiving a representation of the secure model profile from a repository; and wherein the repository comprises a plurality of secure model profiles offering varying specified degrees of accuracy to provide different measurement performance levels.

11. The automated method of claim 1, wherein obtaining the secure model profile comprises receiving a representation of the secure model profile from a repository; and wherein the repository comprises a plurality of secure model profiles corresponding to different respective types of edible oil.

12. The automated method of claim 1, wherein the secure model profile is universal to at least two different respective types of edible oil.

13. The automated method of claim 12, wherein the at least two different respective types of edible oil include at least two of canola oil, soybean oil, corn oil, or combinations thereof.

14. The automated method of claim 1, wherein the secure model profile comprises a set of regression coefficients.

15. The automated method of claim 14, wherein transforming the reflectance data comprises:
converting the reflectance data into absorbance data;
adjusting the absorbance data to account for wavelength-dependent scatter;
determining respective derivative values of the adjusted absorbance data corresponding to discrete wavelength values within the specified range of wavelengths; and
multiplying a vector defining the regression coefficients by the derivative values to obtain the value indicative of the characteristic.

16. The automated method of claim 1; wherein the specified range of infra-red wavelengths includes a near-infrared (NIR) range of wavelengths from about 700 nanometers to about 1100 nanometers.

17. The automated method of claim 1, wherein obtaining the secure model profile corresponding to the characteristic being assessed, transforming the reflectance data using the secure model profile to generate the value corresponding to the characteristic and applying the criterion to the value to provide the representation of the characteristic for presentation the user are performed using a second device communicatively coupled to the spectrometer.

18. The automated method of claim 17, wherein the second device is wirelessly communicatively coupled to the spectrometer.

19. The automated method of claim 17, wherein the second device is located remotely with respect to the spectrometer, the second device communicatively coupled to the spectrometer through an intermediary device.

20. The automated method of claim 19, wherein the second device comprises a network-connected computing and storage system; and
wherein the intermediary device comprises a mobile device.

* * * * *